United States Patent [19]
Dreyfuss et al.

[11] Patent Number: 5,643,869
[45] Date of Patent: Jul. 1, 1997

[54] PIPECOLIC ACID-CONTAINING PEPTOLIDES, THEIR PREPARATION AND PHARMACEUTICAL COMPOSITIONS CONTAINING THEM

[75] Inventors: Michael Morris Dreyfuss, Basel, Switzerland; Gerhard Emmer; Maximilian Grassberger, both of Vienna, Austria; Klaus Rüedi, Therwil; Hans Tscherter, Allschwil, both of Switzerland

[73] Assignee: Sandoz Ltd., Basel, Switzerland

[21] Appl. No.: 446,983

[22] Filed: May 22, 1995

Related U.S. Application Data

[63] Continuation of Ser. No. 187,929, Jan. 27, 1994, abandoned, which is a continuation of Ser. No. 874,277, Apr. 24, 1992, abandoned, which is a continuation of Ser. No. 411,336, Sep. 22, 1989, abandoned.

[30] Foreign Application Priority Data

Sep. 23, 1988 [DE] Germany ............... 38 32 362.1

[51] Int. Cl.⁶ ............ A61K 38/00; C07K 5/12; C07K 7/06
[52] U.S. Cl. .............. 514/9; 514/11; 530/317
[58] Field of Search .............. 530/317; 514/9, 514/11

[56] References Cited

U.S. PATENT DOCUMENTS 3,585,111  6/1971  Coats et al. ............... 195/81

OTHER PUBLICATIONS

Br. J. Cancer (1992) 65, 11–18.
Cancer Res. vol. 51, pp. 4226–4233 (1991).
Br. J. Cancer (1988) 57, 254–258.
Br. J. Cancer (1987) 56, 55–67.

*Primary Examiner*—Cecilia J. Tsang
*Assistant Examiner*—S. G. Marshall
*Attorney, Agent, or Firm*—Robert S. Honor; Melvyn M. Kassenoff; Thomas O. McGovern

[57] ABSTRACT

Pipecolic acid-containing peptolides wherein the peptidic backbone is of at least 9 α-amino acid residues joined together by peptide bonds, particularly the compounds of formula I

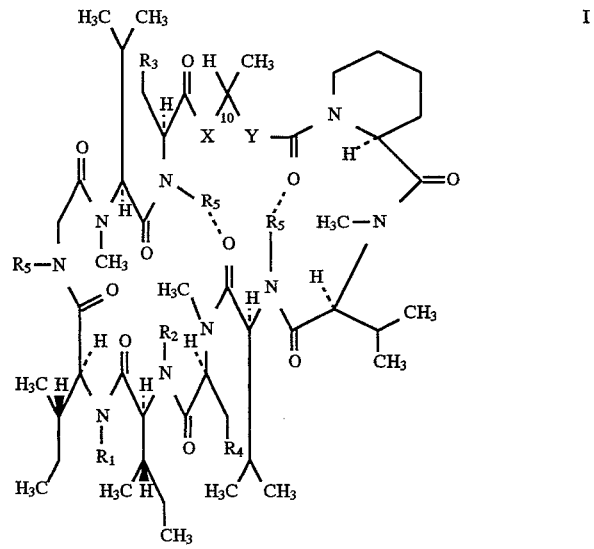

wherein the substituents have various significances, are disclosed.

They can be prepared by isolation or derivation from an appropriate microorganism strain such as S 42508/F (NRRL 15761).

They have interesting pharmacological, e.g. antifungal, chemotherapeutic drug resistance reversing and to some extent immunosuppressant and antiinflammatory properties.

6 Claims, No Drawings

PIPECOLIC ACID-CONTAINING PEPTOLIDES, THEIR PREPARATION AND PHARMACEUTICAL COMPOSITIONS CONTAINING THEM

This is a continuation of application Ser. No. 08/187,929, filed Jan. 27, 1994, which in turn is a continuation of application Ser. No. 07/874,277, filed Apr. 24, 1992, which in turn is a continuation of application Ser. No. 07/411,336, filed Sep. 22, 1989, all of which are now abandoned.

The invention relates to the field of natural products chemistry, in particular of peptolides.

The invention concerns novel pipecolic acid-containing peptolides wherein the peptidic backbone includes at least 9 α-amino acid residues joined together by peptide bonds, hereinafter referred to as "the compounds of the invention", especially such pipecolic acid-containing cyclopeptolides.

The invention concerns in particular a compound of formula I

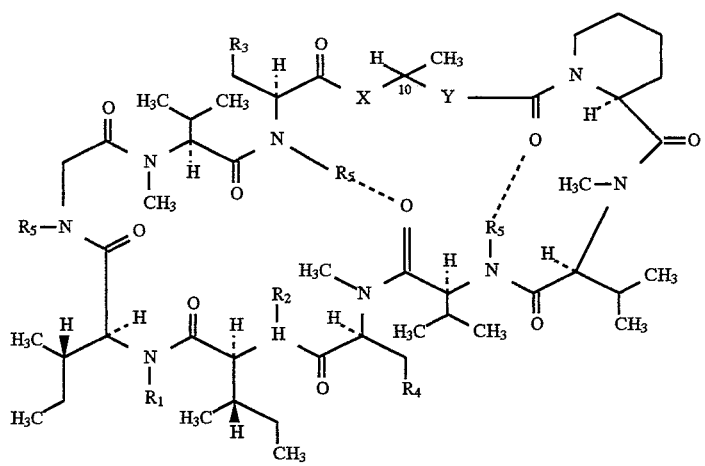

wherein one of $R_1$ and $R_2$ is methyl and the other is hydrogen or methyl;

$R_3$ is: cyclohexyl; cyclohexenyl; cyclohexadienyl; or phenyl substituted in the para position by a group —$OR_6$ wherein —$OR_6$ is hydroxy, alkoxy, alkenyloxy, acyloxy, geranyloxy, alkoxycarbonyloxy, aralkoxycarbonylmethoxy, aralkoxy or aralkoxy substituted by a lover alkyl group or halogen;

$R_4$ is: hydrogen; carboxy; alkoxycarbonyl optionally mono- or plurisubstituted by aryl; alkenyloxycarbonyl; alkeninyloxycarbonyl; benzyloxycarbonyl; aryloxycarbonyl; trimethylsilylethoxycarbonyl; formyl; alkylcarbonyl; aralkylcarbonyl; a group of formula —CONHCH($R_7$)COOR$_8$ or

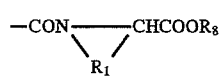

wherein $R_7$ is the side chain moiety of a naturally-occurring amino acid and $R_8$ is alkyl optionally mono- or plurisubstituted by aryl; alkenyl; alkeninyl; benzyl; aryl; or trimethylsilylethyl;

a group selected from the following six ring structures:

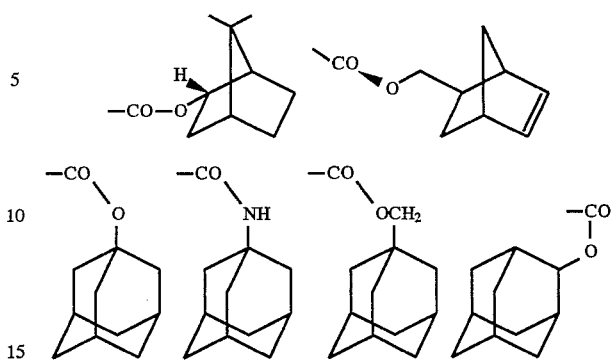

a group —$CONR_9R_{10}$ wherein either $R_9$ and $R_{10}$ independently are: benzhydryl; alkyl; aralkoxycarbonylalkyl; trimethylsilylmethyl; furylmethyl; alkenyl; hydroxyalkyl; alkoxyalkyl; alkoxycarbonylalkyl; aryl; aryl substituted by an alkyl or an amino moiety or by halogen; trialkylsilyloxyalkyl; alkoxy; hydrogen; a group selected from the following six ring structures:

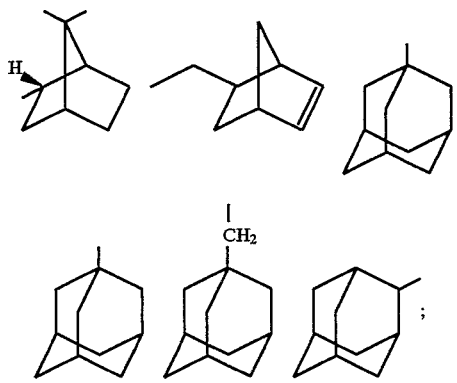

or dialkylaminoalkyl;

or $R_9$ and $R_{10}$ together with the nitrogen atom to which they are bound form a saturated, optionally substituted 5- or 6-membered ring;

hydroxymethyl; alkoxymethyl; acyloxymethyl optionally substituted in the acyl part; dialkylaminomethyl; diacylaminomethyl optionally substituted in the acyl part(s); acyl (alkyl)aminomethyl optionally substituted in the acyl part; sulfhydrylmethyl; alkylthiomethyl; acylthiomethyl optionally substituted in the acyl part; alkylmethyl; alkenylmethyl; azidomethyl; methyl; halogenomethyl; a group of

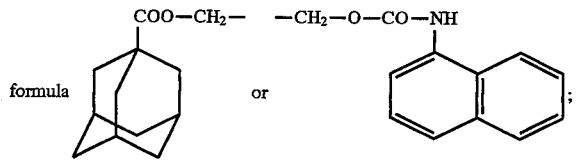

cyano; 2-(alkoxycarbonyl)ethyl; or 2-(alkoxycarbonyl)ethenyl;

all three $R_5$ groups are identical and are hydrogen or methyl; X is oxygen or imino; and Y is a direct bond or a group —CONHCH($CH_3$)—;

with the proviso that when $R_5$ is methyl, then $R_1$ and $R_2$ are methyl and $R_4$ is other than carboxy.

The carbon atom in the 10 position indicated in formula I can be in the L- or the D-configuration.

The hydrogen bonds connecting $R_5$ with oxygen and marked by a dotted line in formula I exist only when $R_5$ is hydrogen.

The cyclopeptolide ring backbone in formula I includes 9, 10 [when either X is imino or Y is a group —CONHCH($CH_3$)—] or 11 [when both X is imino and Y is a group —CONHCH($CH_3$)—] α-amino acid moieties. The α-amino acid moieties are the moiety of naturally-occurring amino acids and include a pipecolic acid residue. The alanyl residue defined when X is imino can be in the L- or the D-configuration at the α-carbon atom in the 10 position in formula I, preferably the L-configuration. The alanyl residue defined when Y is a group —CONH($CH_3$)— can also be in the L- or the D-configuration at the α-carbon atom.

When X is oxygen the cyclopeptolide ring backbone also includes a lactoyl residue, which can be in the L- or in the D-configuration, preferably in the L-configuration at the carbon atom in the 10 position in formula I.

Formula I may alternatively be represented as formula I'

$R_5$Gly—MeVal—A—B—Pec—MeVal—$R_5$Val—D—$R_2$Ile—$R_1$Ile     I'

wherein

Me is methyl attached at the nitrogen atom of the carbamoyl group, $R_1$, $R_2$ and $R_5$ are as defined above and are attached at the nitrogen atom of the carbamoyl group, A is

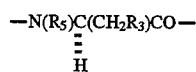

wherein $R_3$ and $R_5$ are as defined above,

B is —X—CH($CH_3$)—Y— wherein X and Y are as defined above, Pec is L-pipecoloyl and D is —N($CH_3$)CH($CH_2R_4$)CO— wherein $R_4$ is as defined above and the asymmetric carbon atom has the S-configuration.

The compounds of formula I can exist in free form or where appropriate in salt, e.g. anionic or acid addition salt form. Salt forms may be recovered from the free form in known manner and vice-versa.

$R_1$ and $R_2$ preferably are identical.

$R_3$ preferably is phenyl substituted as defined above.

$R_4$ preferably is hydrogen; carboxyl; alkoxycarbonyl optionally mono- or plurisubstituted by aryl; alkenyloxycarbonyl; trimethylsilylethoxycarbonyl; formyl; (1- or 2-adamantyl)oxycarbonyl; (1-adamantyl)methoxycarbonyl; bornyloxycarbonyl; —CONR$_9$R$_{10}$ wherein either $R_9$ and $R_{10}$ independently are benzhydryl, alkyl, aralkoxycarbonylalkyl, trimethylsilylmethyl, furylmethyl, alkenyl, hydroxyalkyl, alkoxycarbonylalkyl, aryl, aryl substituted by halogen, trialkylsilyloxyalkyl, hydrogen, 1- or 2-adamantyl or dialkylaminoalkyl, or wherein $R_9$ and $R_{10}$ together with the nitrogen atom to which they are bound form a saturated, optionally substituted 5- or 6-membered ring; hydroxymethyl; acyloxymethyl optionally substituted in the acyl part; azidomethyl; methyl; halogenomethyl; 2-(alkoxycarbonyl)ethyl; or 2-(alkoxycarbonyl)ethenyl.

$R_4$ especially is a group —CONR$_9$R$_{10}$ or alkoxycarbonyl.

$R_5$ preferably is hydrogen or, alternatively, methyl; it especially is hydrogen.

X preferably is oxygen or, alternatively, imino; it especially is oxygen.

Y preferably is a direct bond or, alternatively, a group —CONHCH($CH_3$)—; it especially is a direct bond.

Alkoxy as such or as part of a substituent preferably is of 1 to 4 carbon atoms. Alkenyloxy preferably is of 3 to 5 carbon atoms. Acyloxy preferably is of 2 to 5 carbon atoms in the alkylene portion thereof. In aryl as a substituent or as part of a substituent the aryl group preferably is phenyl. When it is substituted it preferably is monosubstituted, preferably in the para position. When it is plurisubstituted it preferably is disubstituted, preferably in the meta and para positions. Aryl preferably is unsubstituted. Halogen preferably is of atomic number of from 9 to 35, it preferably is chlorine or bromine.

Alkoxycarbonyl preferably is of 2 to 10 carbon atoms, especially of 4 to 9 carbon atoms. Alkenyloxycarbonyl preferably is of 4 to 10 carbon atoms, especially of 4 to 6 carbon atoms.

A naturally-occurring amino acid is any amino acid found in nature, preferably an amino acid found in proteins unless indicated otherwise, especially an α-amino acid, and includes e.g. glycine, proline and serine.

Alkyl preferably is of 1 to 6 carbon atoms. Lower alkyl preferably is of 1 to 4 carbon atoms, especially methyl. Alkyl of 1 to 4 carbon atoms preferably is methyl, isopropyl or tert-butyl. Alkenyl preferably is of 3 to 5 carbon atoms, it especially is allyl. Hydroxyalkyl preferably is of 1 to 4 carbon atoms, it especially is hydroxymethyl; however, when it is bound to a nitrogen atom it preferably is of 2 to 6 carbon atoms and the hydroxy group preferably is separated from the nitrogen atom by at least 2 carbon atoms. Dialkylaminoalkyl preferably is of 1 to 4 carbon atoms in the alkyl parts and of 2 to 4 carbon atoms in the aminoalkyl part, it especially is 3-(dimethylamino)propyl. Furylmethyl preferably is 2-furylmethyl. Alkoxycarbonylalkyl preferably is of 1 to 4 carbon atoms in the alkoxy part and of 2 to 4 carbon atoms in the carbonylalkyl part. Trialkylsilyloxyalkyl preferably is of 1 to 4 carbon atoms in the alkyl parts bound to the silicium atom and of 2 to 4 carbon atoms in the alkylene part.

A saturated, optionally substituted 5- or 6-membered ring formed by $R_9$ and $R_{10}$ together with the nitrogen atom to which they are bound preferably is 6-membered, it preferably is 1-piperidinyl. It preferably is unsubstituted.

Acyl as such or as part of a substituent preferably is alkylcarbonyl, preferably of altogether 2 to 4 carbon atoms. Optionally substituted acyloxymethyl preferably is of 1 to 4 carbon atoms in the acyloxy part; if substituted it preferably is substituted at the ω carbon atom, preferably by carboxy or 2-carboxyphenyl.

Alkyl as part of a substituent such as dialkylaminomethyl preferably is of 1 to 4 carbon atoms, it especially is methyl. Halogenomethyl preferably is chloromethyl.

When $R_4$ is a group —$CONR_9R_{10}$ one of $R_9$ and $R_{10}$ especially is hydrogen and the other is as defined above, especially trimethylsilylmethyl. When $R_4$ is alkoxycarbonyl it especially is tert-butoxycarbonyl.

A subgroup of compounds of formula I is the compounds of formula Ide or $R_9{}^d$ and $R_{10}{}^d$ together with the nitrogen atom to which they are bound form a saturated, optionally substituted 5- or 6-membered ring;
acyloxymethyl substituted in the acyl part; diacyloxyaminomethyl substituted in the acyl part(s); acyl(alkyl)aminomethyl substituted in the acyl part; acylthiomethyl substituted in the acyl part;
2-(alkoxycarbonyl)ethyl; or
2-(alkoxycarbonyl)ethenyl;
$R_5$, X and Y are as defined above, with the proviso that when $R_5$ is methyl then $R_1$ and $R_2$ are methyl and $R_4$ is other than carboxy.

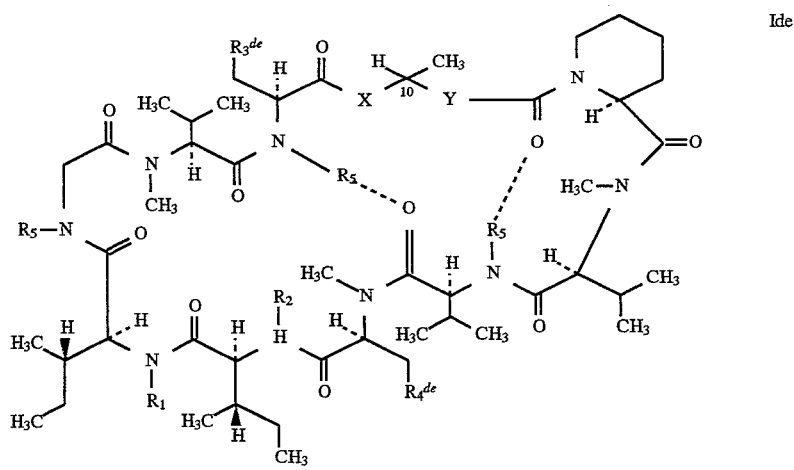

Ide wherein
$R_1$ and $R_2$ are as defined above;
$R_3{}^{de}$ with the exception of aralkoxy substituted by a lower alkyl group or halogen has the significance indicated above for $R_3$;
$R_4{}^{de}$ has the significance indicated above for $R_4$, with the following exceptions: hydrogen; alkoxycarbonyl mono- or plurisubstituted by aryl;
a group —$CONR_9{}^dR_{10}{}^d$ wherein either $R_9{}^d$ and $R_{10}{}^d$ independently are: aralkoxycarbonylalkyl; alkoxycarbonylalkyl; unsubstituted aryl other than phenyl; aryl substituted by an alkyl or an amino moiety or by halogen; trialkylsilyloxyalkyl; or a group selected from the following six ring structures:

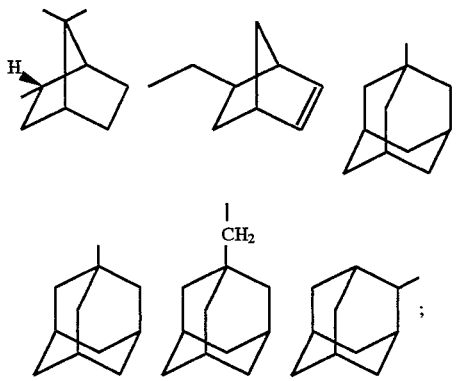

A further subgroup of compounds of formula I is the compounds of formula Ide minus the compounds of formula Ia, i.e. the compounds of formula Ide as defined above with the further proviso that when $R_3{}^{de}$ is para-methoxyphenyl, $R_4{}^{de}$ is carboxyl, $R_5$ is hydrogen, X is oxygen and Y is a direct bond, then the carbon atom in the 10 position in formula I is in the L-configuration.

A further subgroup of compounds of formula I is the compounds of formula Iss

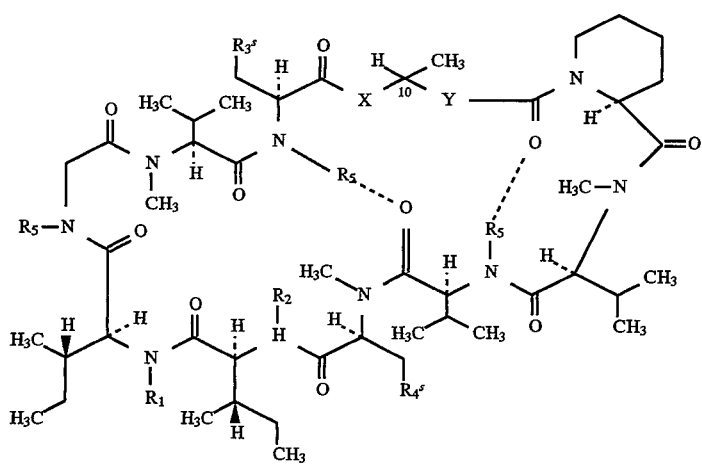

wherein

R₁, R₂, R₅, X and Y are as defined above;

$R_3^s$ is phenyl substituted in the para position by a group —$OR_6^s$ wherein —$OR_6^s$ is selected from hydroxy, alkoxy of 1 to 4 carbon atoms, alkenyloxy of 3 to 5 carbon atoms wherein the double bond is separated from the oxygen atom by at least 2 carbon atoms, acyloxy of 2 to 5 carbon atoms, geranyloxy, phenylalkoxycarbonylmethoxy of 7 to 9 carbon atoms in the phenylalkoxy part, phenylalkoxy of 7 to 9 carbon atoms or phenylalkoxy of 7 to 9 carbon atoms monosubstituted by halogen of atomic number of from 9 to 35;

$R_4^s$ is: hydrogen; carboxy; alkoxycarbonyl of 2 to 10 carbon atoms; alkenyloxycarbonyl of 4 to 10 carbon atoms wherein the double bond is separated from the oxygen atom by at least 2 carbon atoms; benzyloxycarbonyl; benzhydryloxycarbonyl; phenoxycarbonyl; trimethylsilylethoxycarbonyl; formyl; a group of formula —$CONHCH(R_7^s)COOR_8^s$ or

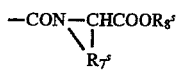

wherein $R_7^s$ is hydrogen, isopropyl or —(CH₂)₃— and
$R_8^s$ is alkyl of 1 to 4 carbon atoms or benzyl; a group selected from the following five ring structures:

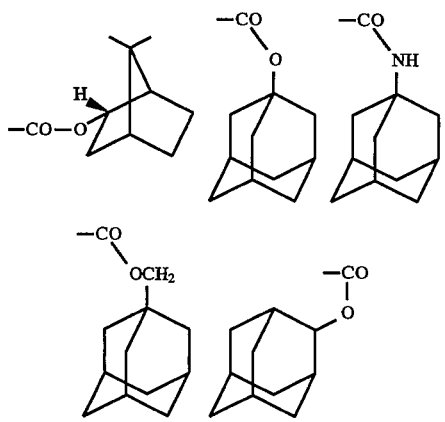

a group —$CONR_9^s R_{10}^s$ wherein
either one of $R_9^s$ and $R_{10}^s$ is hydrogen or alkyl of 1 to 4 carbon atoms and the other is: benzhydryl; alkyl of 1 to 6 carbon atoms; phenylalkoxycarbonylalkyl of 6 to 9 carbon atoms in the phenylalkoxy part and of 2 to 4 carbon atoms in the carbonylalkyl part; trimethylsilylmethyl; furylmethyl; alkenyl of 3 to 5 carbon atoms wherein the double bond is separated from the nitrogen atom by at least 2 carbon atoms; hydroxyalkyl of 2 to 6 carbon atoms wherein the hydroxy group is separated from the nitrogen atom by at least 2 carbon atoms; alkoxycarbonylalkyl of 1 to 4 carbon atoms in the alkoxy part, of 2 to 4 carbon atoms in the carbonylalkyl part and wherein the oxygen atoms are separated from the nitrogen atom by at least 2 carbon atoms; phenyl optionally monosubstituted by halogen of atomic number of from 9 to 35; trialkylsilyloxyalkyl of 1 to 4 carbon atoms in the alkyl parts bound to the silicium atom, of 2 to 6 carbon atoms in the alkylene part and wherein the oxygen atom is separated from the nitrogen atom by at least 2 carbon atoms; 1-adamantyl; or dialkylaminoalkyl of independently 1 to 4 carbon atoms in the alkyl parts, of 2 to 4 carbon atoms in the aminoalkyl part and wherein the nitrogen atoms are separated by at least 2 carbon atoms;

or $R_9^s$ and $R_{10}^s$ together with the nitrogen atom to which they are bound form a 1-piperidinyl ring;

hydroxymethyl; acyloxymethyl of 1 to 4 carbon atoms in the acyloxy part and optionally substituted at the ω carbon atom by carboxy or 2-carboxyphenyl; azidomethyl; halogenomethyl wherein the halogen atom is of atomic number of from 9 to 35; 2-(alkoxycarbonyl)ethyl of 1 to 4 carbon atoms in the alkoxy part; or 2-(alkoxycarbonyl)ethenyl of 1 to 4 carbon atoms in the alkoxy part;

with the proviso that, when R₅ is methyl, then R₁ and R₂ are methyl and $R_4^s$ is other than carboxy.

The compounds of the invention can be obtained according to standard methods, e.g. by cultivation of an appropriate pipecolic acid-containing peptolide-producing microorganism strain, followed by isolation and where indicated appropriate chemical derivation. An appropriate microorganism strain is e.g. as described for process variant a) hereunder. Preferred is a strain producing a cyclic pipecolic acid-containing peptolide, such as S 42508/F (NRRL 15761).

Thus a compound of formula I can be obtained by a process comprising a) for the preparation of a compound of formula Ia

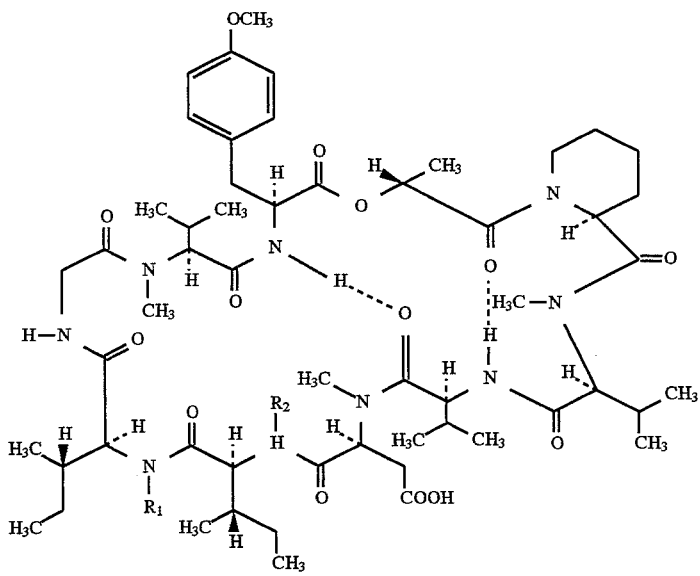
wherein $R_1$ and $R_2$ are as defined above, cultivating an appropriate microorganism strain and isolating the compounds of formula Ia from the resultant culture;
b) for the preparation of a compound of formula Ib
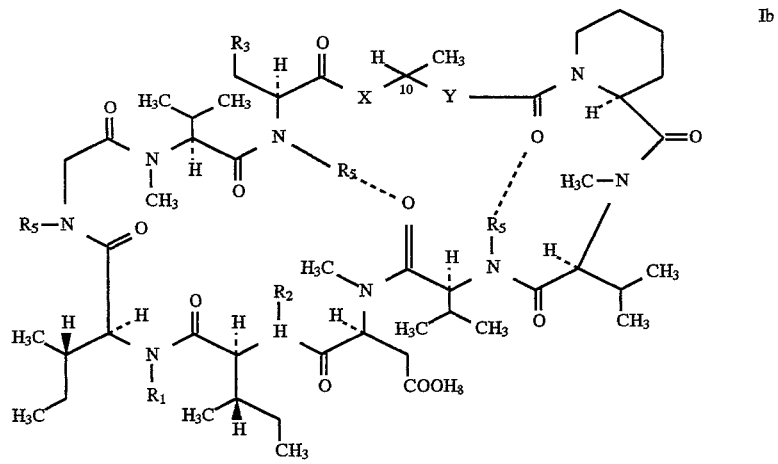
wherein the substituents are as defined above, appropriately esterifying a corresponding compound of formula Ic

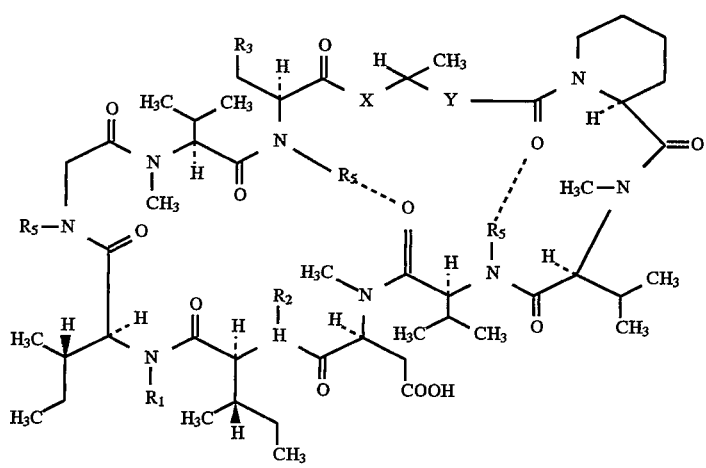
wherein the substituents are as defined above;
c) for the preparation of a compound of formula Id
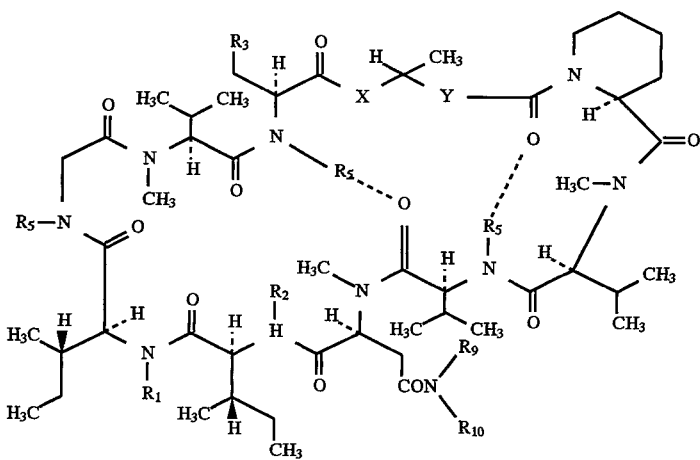
wherein the substituents are as defined above, appropriately amidating a corresponding compound of formula Ic;
d) for the preparation of a compound of formula Ie
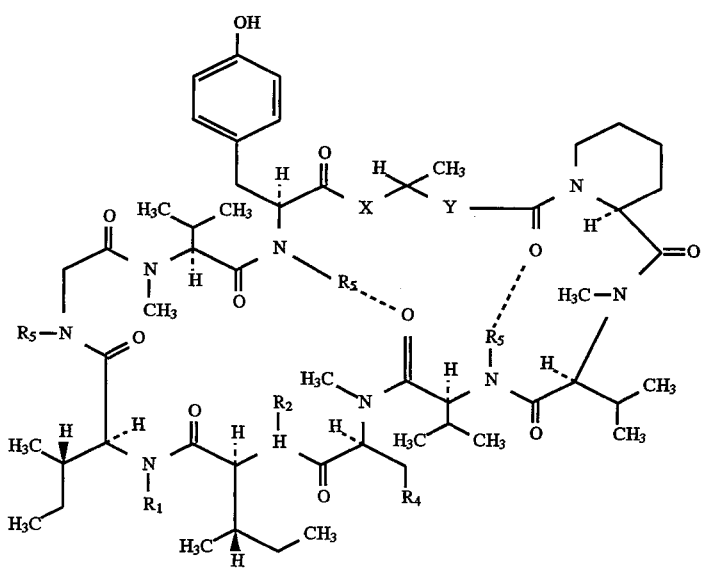

wherein the substituents are as defined above, appropriately splitting off the ether group from a corresponding compound of formula If

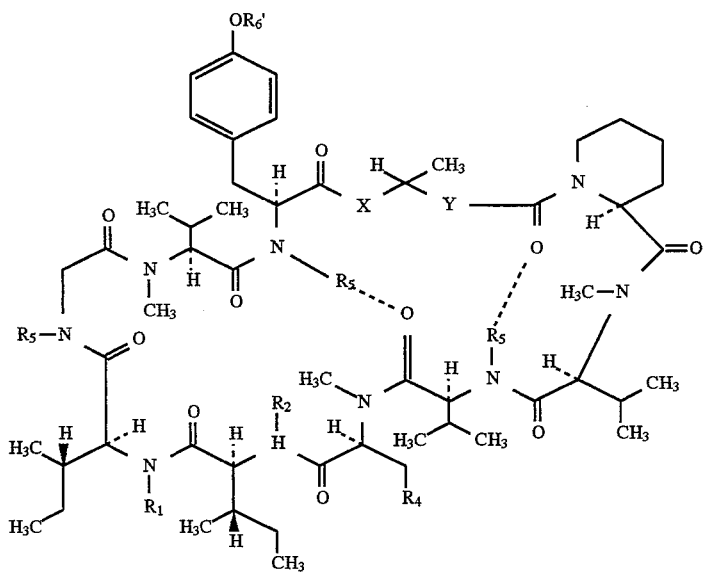

If wherein $R_6'$ with the exception of hydrogen has the significance
indicated above for $R_6$ and the remaining substituents are as defined above;

e) for the preparation of a compound of formula Ig

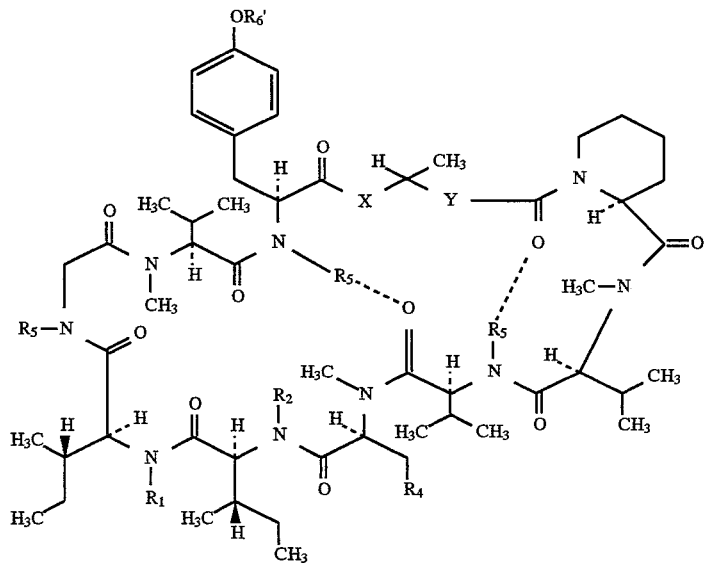

Ig wherein the substituents are as defined above, appropriately introducing a group $R_6'$ into a corresponding compound of formula Ie;

f) for the preparation of a compound of formula Ih (=I)

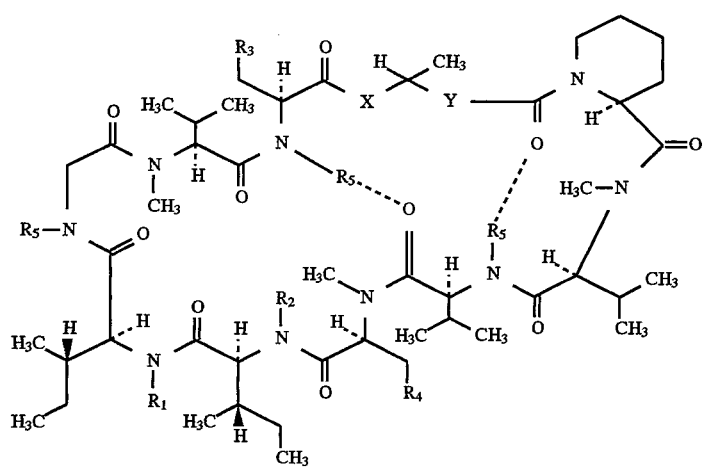
Ih
wherein the substituents are as defined above, appropriately cyclising a corresponding compound of formula II
wherein $R_6''$ is alkylmethyl of altogether at least 3 carbon atoms and
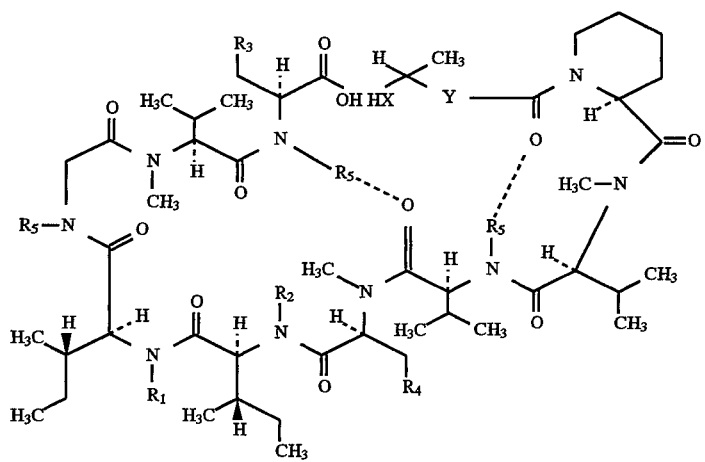
II
wherein the substituents are as defined above;
g) for the preparation of a compound of formula Ij
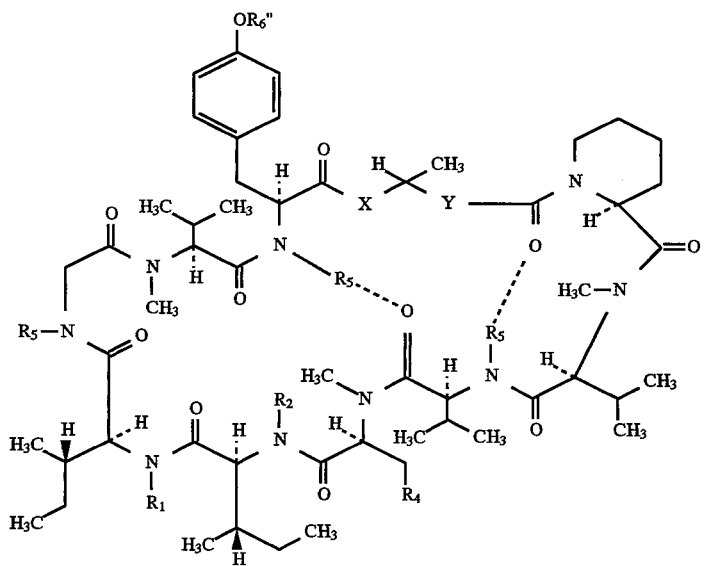
Ij the remaining substituents are as defined above, appropriately hydrogenating a corresponding compound of formula Ik

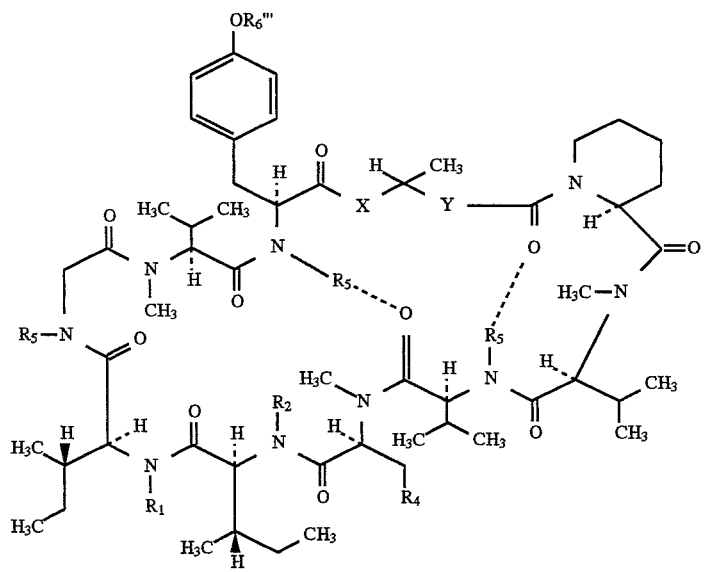

Ik wherein $R_6'''$ is alkenylmethyl of altogether at least 3 carbon atoms and the remaining substituents are as defined above;

h) for the preparation of a compound of formula Im

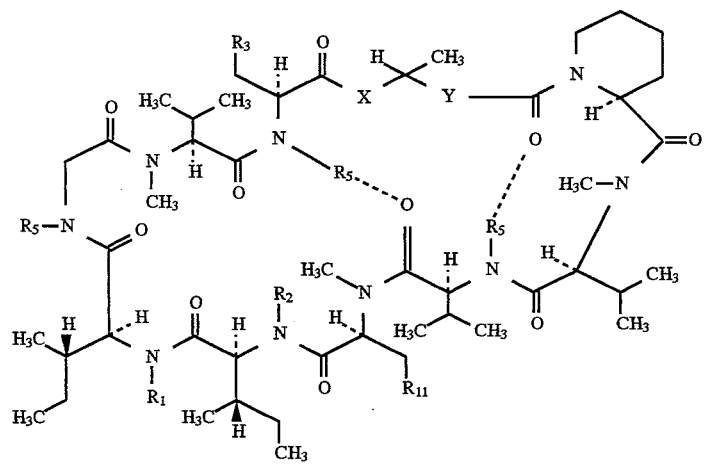

Im wherein $R_{11}$ is formyl or hydroxymethyl and the remaining substituents are defined above, appropriately reducing a corresponding compound of formula i) for the preparation of a compound of formula In

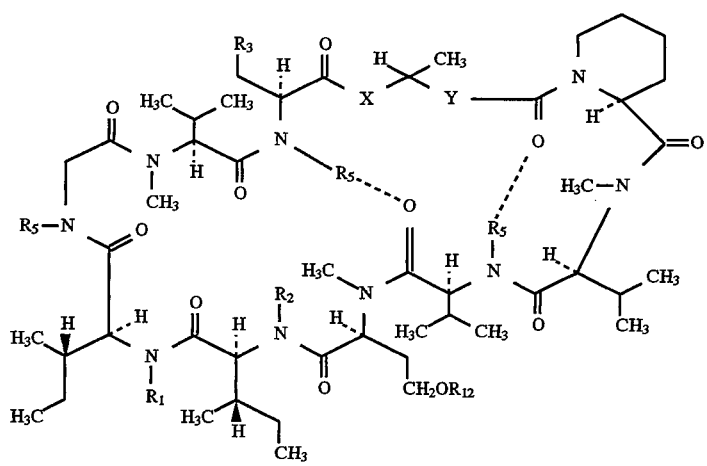
In
wherein $R_{12}$ is optionally substituted acyl and
the remaining substituents are as defined above, appropriately acylating a corresponding compound of formula Io
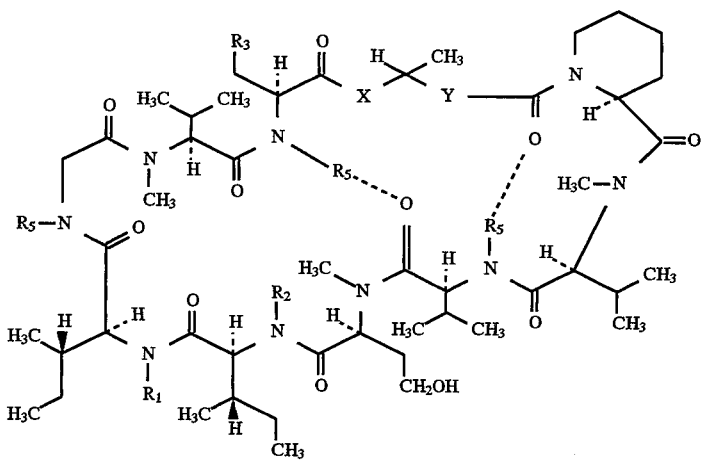
Io
wherein the substituents are as defined above;
j) for the preparation of a compound of formula Ip
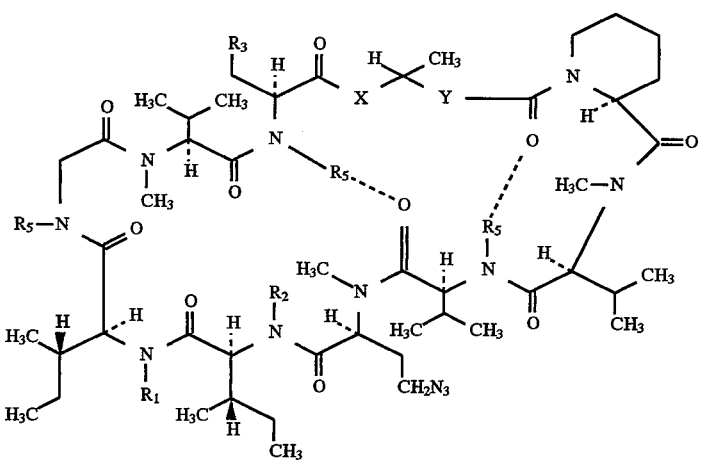
Ip wherein the substituents are as defined above, appropriately converting to the azide a corresponding compound of formula Io;

k) for the preparation of a compound of formula Iq

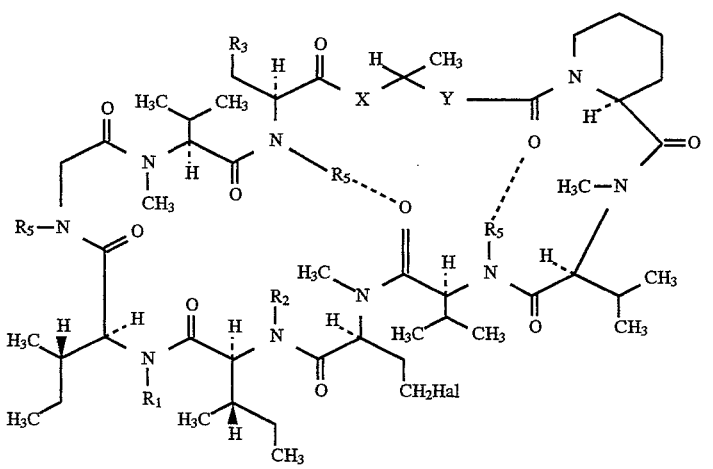

wherein Hal is halogen and
the remaining substituents are as defined above, appropriately halogenating a corresponding compound of formula Io;

m) for the preparation of a compound of formula Ir

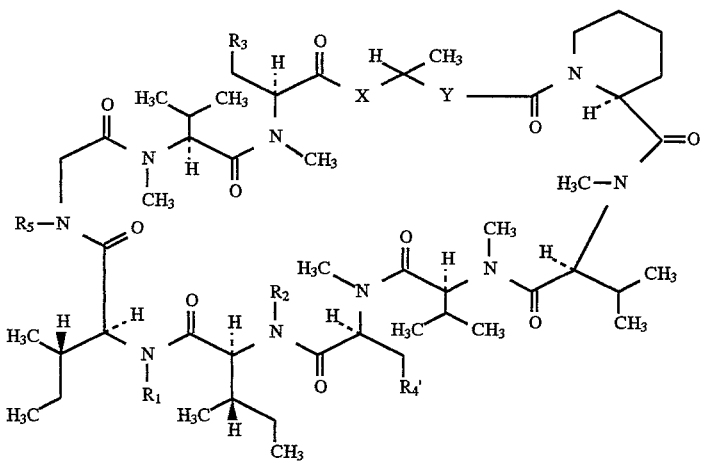

wherein $R_4'$ is alkoxycarbonyl optionally mono- or plurisubstituted by aryl; alkenyloxycarbonyl; alkeninyloxycarbonyl; benzyloxycarbonyl; aryloxycarbonyl; or trimethylsilylethoxycarbonyl and the remaining substituents are as defined above, appropriately permethylating a corresponding compound of formula Is

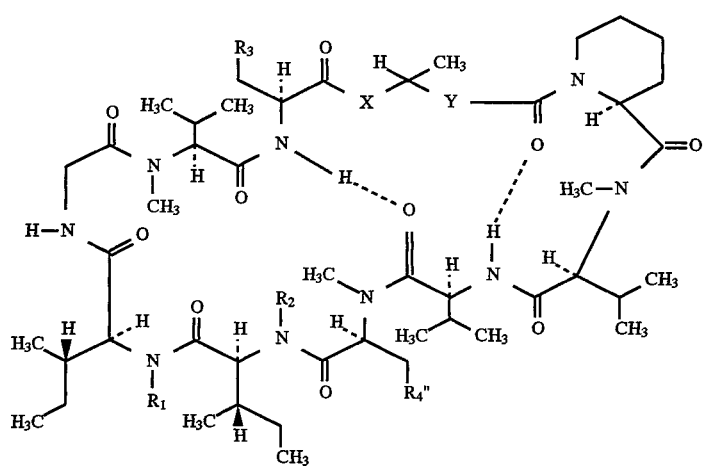

wherein $R_4''$ is carboxy or a group $R_4'$ as defined above and the remaining substituents are as defined above;

n) for the preparation of a compound of formula It

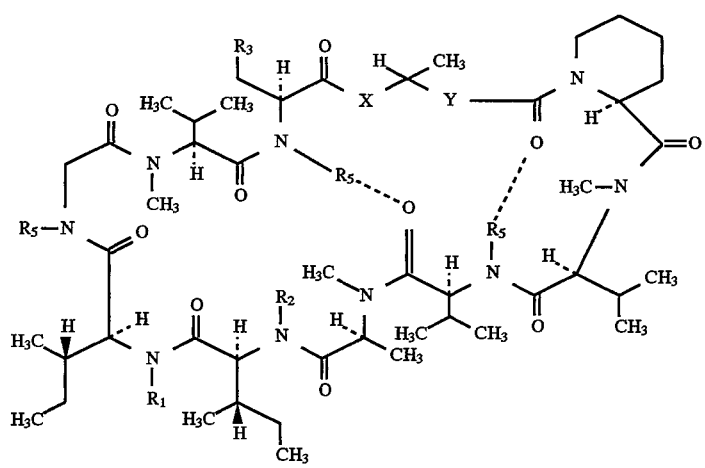

wherein the substituents are as defined above, appropriately decarboxylating a corresponding compound of formula Ic;

o) for the preparation of a compound of formula Iu

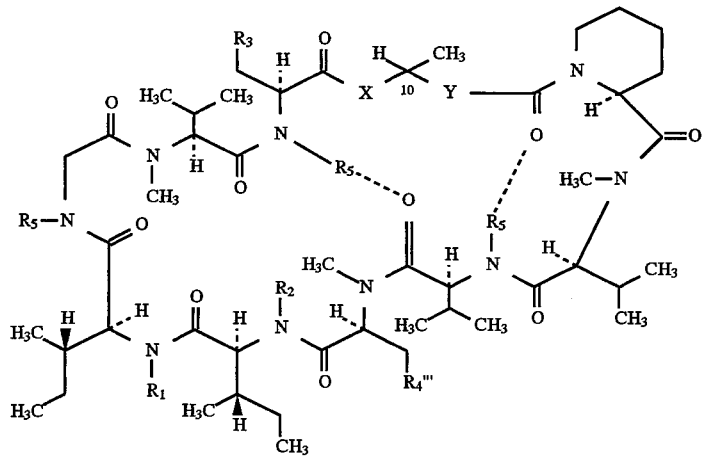

wherein $R_4'''$, is 2-(alkoxycarbonyl)ethenyl and the remaining substituents are as defined above, appropriately reacting a corresponding compound of formula Iv

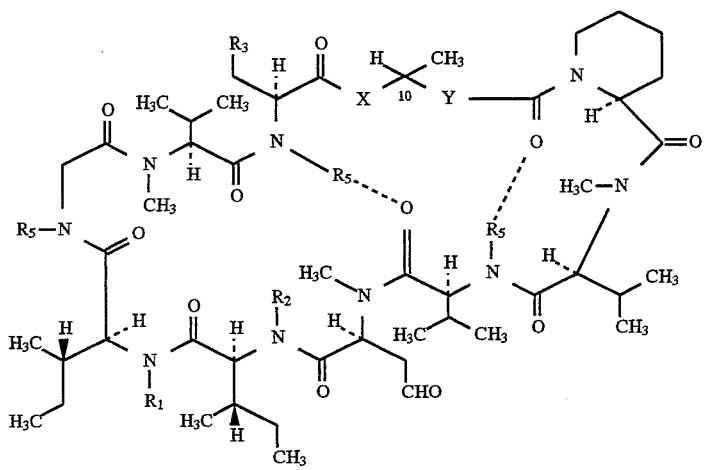

wherein the substituents are as defined above, with a corresponding compound having an activated methylene group; or p) for the preparation of a compound of formula Iw

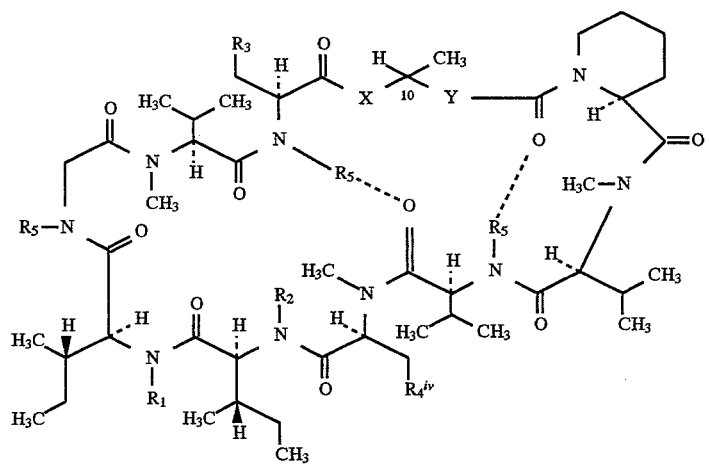

wherein $R_4^{iv}$ is 2-(alkoxycarbonyl)ethyl and the remaining substituents are as defined above, appropriately hydrogenating a corresponding compound of formula Iu;

whereby for all above process variants and as a further process variant any hydroxy and/or carboxy group(s) may be in protected form and thereafter the protecting group(s) split off.

In a subgroup of compounds of formula Iss $R_4^s$ is other than carboxy. In a further subgroup $R_1$ and $R_2$ are methyl. In a further subgroup $R_5$ is hydrogen. In a further subgroup $R_4^s$ is other than carboxy, $R_3^s$ is other than p-methoxyphenyl, $R_5$ is other than hydrogen, X is other than oxygen, Y is other than a direct bond and the carbon atom in 10 position does not have the D-configuration, i.e. the compounds of formula Iss are in this subgroup other than compounds of formula Ia.

In a further subgroup of compounds of formula Iss $R_4^s$ is one of the ester groups defined above for $R_4^s$. In a further subgroup $R_4^s$ is a group —$CONR_9^sR_{10}^s$. In a further subgroup $R_3^s$ is p-hydroxyphenyl. In a further subgroup $R_3^s$ is phenyl substituted in the para position by a group —$OR_6^s$ other than hydroxy. In a further subgroup $R_3^s$ is phenyl substituted in the para position by a group —$OR_6^{41}$. In a further subgrroup $R_4^s$ is a group $R_{11}$. In a further subgroup $R_4^s$ is group —$CH_2OR_{12}$. In a further subgroup $R_4^{11}$ is a group —$CH_2N_3$. In a further subgroup $R_4^s$ is a group —$CH_2Hal$. In a further subgroup $R_4^5$ is a group $R_4'$. In a further subgroup $R_4^s$ is methyl. In a further subgroup $R_4^s$ is a group $R_4'''$. In a further subgroup $R_4^s$ is a group $R_4^{iv}$. In a further subgroup $R_3^s$ and/or $R_4^s$ are in unprotected form.

The above process variants may be effected according to standard procedures. The configuration at the α-carbon atom in the 10 position indicated in formula I and in the alanyl residue defined when Y is a group —CONHCH(CH₃)— remains normally unchanged, except that, when X is oxygen, reaction conditions for cyclization can be chosen which result in inversion of the configuration at the lactoyl moiety (see e.g. the description of process variant f) hereunder and Examples 52 to 63 and 68). On the other hand, after the ring system has been opened reaction conditions may be selected which lead to an inversion of the configuration during intermediate steps and thus from compounds having the D-configuration compounds having the L-configuration can be obtained, and vice-versa (see e.g. the preparation of the starting materials for Example 64). Alternatively, reaction conditions can be chosen which leave the configuration unchanged after the ring system has been opened (see e.g. the preparation of the starting material for Example 65).

Process variant a) (cultivation) may be effected using a microorganism strain from e.g. the Imperfect fungal class, such as S 42508/F. This strain has been deposited on Mar.

29, 1984 with the Agricultural Research Service Patent Culture Collection, 1815 North University Street, Peoria, Ill. 61604, USA under deposit number NRRL 15761 and converted on Jul. 11–12, 1988 to a deposit under the Budapest Treaty.

Characteristics of the strain NRRL 15761:

The fungus strain NRRL 15761 was isolated from dead plant material originating from a rapidly flowing stream in the Black Forest. After two to six weeks incubation on 2% malt extract agar (MA) at incubation temperatures of from 1° to 18° (preferably 4° to 15°), pycnidia are formed. The conidiomates are singular or in closely packed groups, superficial or partially immersed in the medium, globose to subglobose, 200–1300 µm (usually 500–800 µm) in diameter, and when fully developed have one papillate ostiole. The pycnidia wall is 50–250 µm thick (usually 100–200 µm) and consists of many cell layers of the type "textura angularis", which are externally dark brown and towards the centre hyaline. The conidiogenic cells lining the centre of the pycnidia are hyaline, wide to narrow, conical to lageniform, 4–6×5.5–20 µm (usually 4–5×6.5–8.5 µm) and according to light microscopy are phialidic in nature. The conidia are hyaline (massed condidia appear yellowish to beige), filiform, straight to slightly bent, broadest in the middle, pointed at one end and rounded or truncated at the opposite end, septated 0 to 6 times, normally, however, three to four times, and measure 30–42×1.8–2.2 µm (usually 35–39×2–2.2 µm).

According to morphological features and using the diagnostic keys of B. C. Sutton, *The Coelomycetes*, Commonwealth Mycological Institute, Kew, Surrey, England 1980), this sphaeropsidal fungus cannot be unequivocally classified. The features of the conidia, but not those of the conidiogenic cells, nor the multi-layered pycnidia wall, conform with the genus Septoria sacc.

The following media and tests were used for the physiological characterisation of the fungal strain:

MA: 2% Difco malt extract; 0.4% Difco yeast extract; 2% Difco Agar.

PA: 0.5% pure soya protein (Promine D), 0.1% Difco yeast extract, 2% Difco Agar. Clearing of the medium indicates protein degradation.

SA: 0.4 g soluble starch (Difco), 0.1% Difco yeast extract, 2% agar. Starch degradation can be demonstrated by flooding with KI solutionl CAA: Cellulose-Azure (Calbiochem)-test by R. E. Smith, 1977, *Applied and Environmmental Microbiology* 33 (4) 980–981.

TA: Tween 40 medium by G. Sierra, 1957, *Antonie yon Leeuwenhoek* 23, 15–22. Medium turbidity indicates lipase activity.

Cz: Difco Czapec solution Agar (pH 7.3).

Cz Gall: Difco Czapec solution Agar with 1.5% gallic acid (pH 7.3) according to N. J. Dix, *Trans. Brit. MTcol. Soc.* 73 (2) (1979) 329–336. Growth inhibition on Cz Gall medium compared with Cz is an indication of polyphenoloxidase formation (G. Lindeberg, *Svensk Botanisk Tidskrift* 43 [1949] 438–447).

Syr: Identification of lactase and peroxidase according to the method of J. M Harkin and J. R. Obst, *Experientia* 29 [1973] 381–508 by covering the cultures with a 0.1% ethanolic syringeldazine solution. Violet-red reaction= positive.

pH media: Medium with pH 2.6 to pH 7.6: MA medium buffered with 0.1M citric acid—0.2M $Na_2HPO_4$ buffer according to McIlvaine in Data for Biochemical Research, Oxford [1969] 484–485.

Medium with pH 7.0–8.0: MA-medium buffered with 0.2M $Na_2HPO_4$—0.2M $Na_2H_2PO_4$ buffer according to Gomori/Sorensen, *Data for Biochemical Research*, Oxford [1969] 489.

Medium with pH 9.2 to 10.8: MA-medium buffered with 0.1M $Na_2CO_3$—0.1M $NaHCO_3$ buffer according to Delory & King, *Data for Biochemical Research*, Oxford [1060] 496.

Buffer and MA medium are each prepared at double concentration, sterilised separately and combined after sterilisation.

Physiological features of the fungal strain:

Optimum growth temperature on MA: between 18°±1° and 21°≅1° C.

Lower growth limit on MA: 1°±1° C.

Upper growth limit on MA: between 27°±1° and 30°±1° C.

Sporulation on MA: 4°±1° C. to 15°±1° C.: optimal
1°±1° C. and 18°±1° C.: suboptimal
21°±1° C. and higher: no sporulation observed.

Syr. on MA (3 weeks incubation at 21° C.): weakly positive.
Syr. on Cz (3 weeks incubation at 21° C.): weakly positive.
Cz: good growth.
Cz Gall: no growth.
PA: weak proteinase activity.
SA: amylase positive.
CAA: cellulase negative.
TA: lipase weakly positive.
pH media: optimum pH range for growth: pH3.6–6.0
lowest pH range for growth: pH3.0–3.6
highest pH range for growth: pH8.0–9.2.

The novel strain S 42508/F (NRRL 15761) may be cultured at suitable temperatures in various culture media using appropriate nutrients and mineral substances, as aerobic surface or immersion cultures. The invention also concerns fermentation broths which are obtained during cultivation of a producing strain from the class of fungi Imperfecti.

Cultivation thus is effected using known procedures and consists essentially in cultivation of the strain on or in an appropriate medium under suitable growth conditions. The compounds formed, e.g. the compounds of formula Ia are subsequently isolated.

The fermentation medium should mainly contain a utilisable source of carbon and optionally mineral salts and growth factors, whereby all these elements can be added in the form of well-defined products or complex mixtures, as are found in biological products of various origins.

In order to produce the novel compounds of formula Ia strains may also be used which are obtained e.g. by selection or mutation under the influence of ultra-violet rays or X-rays or using other means, e.g. by treating cultures with appropriate chemicals.

As soon as a sufficient amount of the compounds of formula Ia has been produced in the culture the mycelium may be separated from the culture broth and extracted conventional manner, e.g. with an organic solvent which is immiscible with water, such as ethyl acetate, butyl acetate or n-butanol.

Another isolation procedure comprises first homogenising the mycelium portion in the culture broth, e.g. using an Ultraturrax, and obtaining the compounds of formula Ia by extraction with the solvents mentioned. A preferred embodiment comprises separating the broth into mycelium and culture liltrate in a Westfalia clearing separator. The mycelium filtrate is then homogenised with methanol in a Dispax reactor, the biomass is separated and the organic phase is concentrated on water, whilst adding water. Here again extraction is effected using an organic solvent which is immiscible with water, e.g. ethyl acetate or n-butanol, and the extracts are evaporated under vacuum. The portion of the desired metabolites remaining in the culture filtrate can also be extracted using the solvents mentioned above.

The compounds of formula Ia can be isolated and purified from the crude extracts thus obtained by known chromatographic methods. It has proved advantageous to first scour with hexane to remove lipophilic impurities. The compounds of formula Ia can then be isolated and separated from one another by chromatography on silicagel Merck 60 or e.g. silicagel H, or by gel filtration on Sephadex $LH_{20}$, and may be recrystalised from e.g. methanol or diisopropylether.

Process variant b) (esterification) is e.g. effected by dissolving a compound of formula Ic into an inert solvent such as an aromatic hydrocarbon, e.g. benzene or toluence, or in an aliphatic ketone, e.g. acetone and adding the corresponding alcohol, e.g. in the form of the acetal, or the halide. The esterification may e.g. also be effected with a corresponding diazomethane derivative, preferably in an inert solvent such as an aliphatic alcohol, e.g. methanol. The carboxy group may be activated prior to reaction, e.g. with N,N-dimethylchloromethylene/ammonium chloride. In the compounds of formula Ic wherein $R_3$ is para-hydroxyphenyl the phenolic hydroxy group may under appropriate conditions, particularly extended reaction duration, also be brought to react.

Process variant c) (amidation) is e.g. effected by activation of the carboxyl group, e.g. with N,N-dimethylchloromethylene ammonium chloride, after dissolution or suspension with an inert solvent such as acetonitrile, followed by addition of the appropriate amine.

Process variant d) (ether splitting) may e.g. be effected with aluminium iodide using standard methods. A compound of formula If preferably is treated with a freshly prepared solution of aluminium iodide in an inert solvent such as carbon disulfide.

Process variant e) (introduction of a group $R_6'$) may e.g. be effected by using standard etherification or esterification conditions. A compound of formula Ig preferably is dissolved into an inert solvent, e.g. an aliphatic ketone such as acetone. An acid scavenger such as potassium carbonate preferably is used for reaction with a corresponding halogenida or anhydride. Under these conditions an ester group present may simultaneously be split off.

For process variant f) (cyclisation) a compound of formula II may e.g. be dissolved into an inert solvent, e.g. a chlorineted hydrocarbon such as dichloromethane. Reaction takes place upon addition of a cyclisation agent, e.g. dicyclohexylcarbodiimide. For cyclisation of compounds wherein $R_4$ is carboxy, which can e.g. be obtained by ring opening from the compounds of formula Ia, cyclisation preferably is effected with the carboxy group in protected form, such as in tert-butyl or benzyl ester form. Depending on the reaction conditions selected for ring opening, activation and cyclisation, end products of formula I are obtained having the L- or the D-configuration at the carbon atom in the 10 position indicated in formula I. Thus the cyclisation of compounds of formula II wherein X is imino, with activation of the carboxyl group with e.g. dicyclohexylcarbodiimide, occurs normally under conservation of the stereochemical configuration in the compounds of formula II being used. A configuration different from or identical to the configuration in the original cyclic starting material may be selected at an earlier step, such as at the activation step, e.g. at the mesylate step (mesyl chloride/pyridine: retention of the configuration) or at the rosylate step (triphenylphosphine/azidodicarboxylic acid diethyl ester/zinc tosylate: inversion of the configuration). However, in compounds of formula II wherein X is oxygen cyclisation may be effected under inversion of the configuration of the lactoyl moiety. In this situation the hydroxy group of the lactoyl moiety is activated (e.g. with triphenylphosphine/azidodicarboxylic acid diethyl ether) and cyclization is effected under attack of the carboxyl at the activated hydroxyl of the lactoyl moiety, whereby inversion occurs (see e.g. Examples 52 to 63 and 68).

Process variants g) (hydrogenation at the $R_3$ group) and p) (hydrogenation at the $R_4$ group) are effected e.g. with hydrogen and palladium on charcoal. A solvent such as a lower alkanol, e.g. ethanol preferably is used.

In process variant h) (reduction of carboxyl) the carboxyl group preferably is first activated with e.g. N,N-dimethylchloromethylammonium chloride and thereafter reaction is effected with e.g. sodium boranate. Lower temperatures are preferably used, e.g. $-70°$ C. The reaction may be controlled and interrupted at the aldehyde stage or brought to completion to the alcohol.

Process variants i) (acylation), j) (conversion to the azide) and k) (halogenation) may be effected by reaction with corresponding reagents, e.g. by reaction with the appropriate acyl anhydride or, after conversion to the mesylate or rosylate, with appropriate azides or halogenides. For acylation the temperature preferably is about room temperature, and reaction is preferably under basic conditions, e.g. in the presence of dimethylaminopyridine. For conversion to the azide the temperature preferably is from about $0°$ C. to about room temperature, preferably $0°$ to $5°$ C. Again basic conditions, e.g. dimethylaminopyridine, are used. Halogenation preferably is effected at room temperature to about $80°$ C., preferably $50°$ to $60°$ C., preferably in the presence of an organic solvent such as pyridine.

Process variant m) (permethylation) is e.g. effected by reaction with a methyl halogenide in the presence of a strong base such as potassium hydroxide. The temperature preferably is low, e.g. about $-20°$ C. When in the compounds of formula Is $R_1$ and/or $R_2$ is hydrogen and/or $R_4''$ is carboxyl, then corresponding compounds of formula Ir are obtained wherein $R_1$ and $R_2$ are methyl and/or $R_4'$ is methoxycarbonyl.

Process variant n) (decarboxylation) leads to compounds of formula I wherein $R_4$ is hydrogen. The carboxy group preferably is first activated, e.g. by reaction with phenylselenyl hydride. Decarboxylation is effected in a second step, e.g. with tributyl zinc hydride, preferably in an inert solvent such as an aromatic hydrocarbon, e.g. toluene or xylene. Preferably an elevated temperature is used, e.g. the boiling temperature of the reaction mixture.

For process variant o) (formyl conversion) a formyl compound of formula Iv preferably is reacted with a compound having an activated methylene group, e.g. with an appropriate methylenetriphenylphosphorane derivative. The reaction preferably is effected in an inert solvent, such as an aromatic hydrocarbon, e.g. toluene. The temperature preferably is moderate, e.g. room temperature.

The optional deprotection step variant may be used for any of the above process variants a) to p). Any hydroxy and/or carboxy group may be in protected form. For protection standard methods may be used. Deprotection is e.g. effected with aqueous acetonitrile. A preferred hydroxy protecting group is e.g. tert-butyldimethylsilyl. A preferred carboxy protecting group is e.g. 2-(trimethylsilyl)ethyl.

It will be appreciated that in addition to hydroxy groups it may be indicated to transiently protect further substituents if these should be sensitive under the reaction conditions used. Thus e.g. an ester group such as 2-(trimethylsilyl) ethoxycarbonyl or tert-butoxycarbonyl may be viewed as a protected carboxy group, an acyl group as a protected hydroxy group, and a benzyloxy group as a protected phenolic hydroxy group. Further protecting groups may of course appear to be indicated to the skilled worker.

The compounds of formula I may be isolated from the reaction mixture and purified in accordance with known procedures.

The starting materials can be obtained in accordance with known methods.

The compounds of formula II are novel and can be obtained by ring opening from the compounds of formula Is, followed where indicated by appropriate chemical derivatisation.

Thus the compounds of formula II wherein X is imino and Y is a group —CONHCH(CH₃)— can be obtained in accordance with the following reaction scheme (R'= protecting group, e.g. benzyl; R"=activation group, e.g. mesyl):

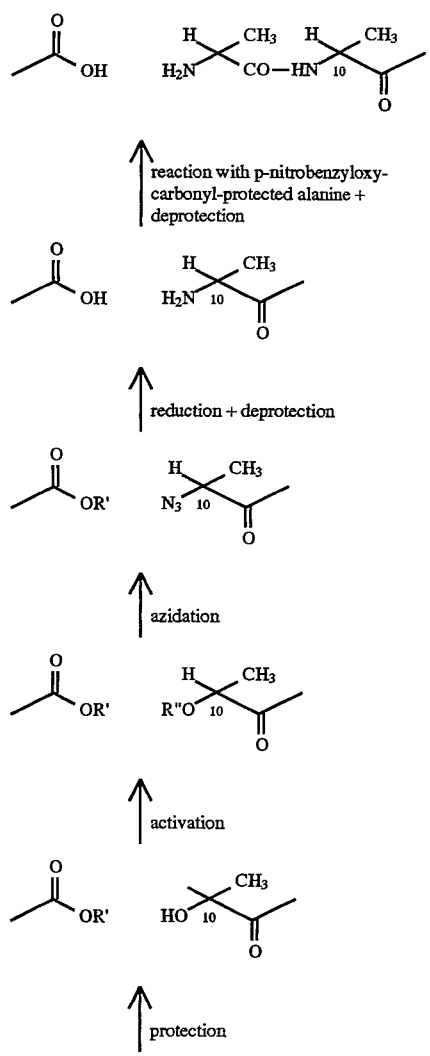

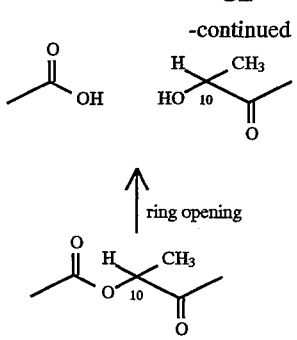

Analogously, the compounds of formula II wherein X is oxygen and Y is a group —CONHCH(CH₃)— can be obtained by reaction with a hydroxy-protected active derivative of lactic acid such as O-acetyl-lactoyl chloride in place of reaction with p-nitrobenzyloxycarbonyl-protected alanine in the above scheme.

The compounds of formula II wherein X is imino and Y is a direct bond can be obtained by omitting the reaction with p-nitrobenzyloxycarbonyl-protected alanine in the above scheme.

The compounds of formula II wherein X is oxygen and Y is a direct bond can be obtained according to the first step (ring opening) in the above scheme.

Ring opening may be effected in conventional manner, e.g. by treatment with lithium hydroxide in an inert solvent or mixture of solvents, e.g. in tetrahydrofuran/water. The further reaction steps in the scheme are also effected in conventional manner. The group R" is selected such that the following conversion to the azide takes place on the desired hydroxy group. Reduction of the azide to the amino group is e.g. effected with hydrogen and palladium on charcoal as a catalyst, using an inert solvent such as an aliphatic alcohol, e.g. ethanol.

Insofar as its preparation is not particularly described herein, a compound used as a starting material is known or may be prepared from known compounds in known manner or analogously to known methods or analogously to methods described in the Examples.

EXAMPLES:

The following Examples illustrate the invention and are not meant to be limitative.

The temperatures are in degrees Centigrade.

The indications regarding the configuration are with respect to the carbon atom in the 10 position indicated in formula I unless indicated otherwise.

The NMR spectra are measured in a 250 MHz apparatus and, where not indicated otherwise, in CDCl₃-solution at room temperature, whereby mixtures of conformers are obtained which interconvert until equilibrium is reached. Only the characteristic signals are indicated. They are proton resonance spectra unless specified otherwise.

Abbreviations:

The amino acids are abbreviated according to usage. Thus e.g. MeIle is N-methyl-L-isoleucine, Tyr(Me) is O-methyl-L-tyrosine, MehSer is N-methyl-L-homoserine, MeAsp (β-O-tert-butyl) is N-methyl-L-aspartic acid esterified by a tert-butyl moiety at the β(=ω) carboxyt group, MeAbu(γ-N₃) is 2-L-N-methylamino-4-azidobutyric acid, Sar is N-methylglycine and Pec is L-pipecolic acid.

Lact=lactoyl, if not indicated otherwise L-lactoyl; tBu= tert-butyl; Bz=benzyl; iPr=isopropyl; Et=ethyl; Me=methyl; Ac=acetyl.

Example 1:
Cyclo-[Pec-MeVal-Val-Me-Asp-MeIle-MeIle-Gly-MeVal-Tyr(Me)-D-Lact]
[$R_1=R_2=$Me; $R_3=$MeO-Phe; $R_4=$COOH; $R_5=$H; X=O; Y=a bond; $C_{10}$ has D-configuration]
Cyclo-[Pec-MeVal-Val-MeAsp-Ile-MeIle-Gly-MeVal-Tyr(Me)-D-Lact]
[$R_1=$Me; $R_2=$H; $R_3$, $R_4$, $R_5$, X, Y, $C_{10}=$as for first compound]
and
cyclo-[Pec-MeVal-Val-MeAsp-MeIle-Ile-Gly-MeVal-Tyr(Me),D,Lact]
[$R_1=$H; $R_2=$Me; $R_3$, $R_4$, $R_5$, X, Y, $C_{10}=$as for first compound ]
[process variant a); cultivation ]
a) Agar starting culture The mycelium suspension used for inoculation is produced from an agar slant culture of the strain S 42508/F which is cultivated for 28 days at 21° on the following agar medium:

| malt extract, liquid | 20 g |
|---|---|
| yeast extract | 4 g |
| agar | 20 g |
| demineralised water | ad 1000 ml |

Prior to sterilisation the pH value is adjusted to 7.5 with NaOH. Sterilisation takes place for 20 minutes at 120°.
b) Preculture The mycelium from the starting culture is suspended in 0.9% sodium chloride solution using a sterile skimmer. 200 ml of preculture medium are inoculated with this suspension in a 500 ml Erlenmeyer flask.

Composition of the preculture medium:

| malt extract, liquid | 20 g |
|---|---|
| yeast extract | 4 g |
| demineralised water | ad 1000 ml | pH 5.6–5.8. Sterilisation: 20 minutes at 120°.

Incubation takes place in a rotary shaker at 180 rpm for 48 hours at 21°.
c) First intermediate culture 50 l of preculture medium in a 75 l steel fermenter are inoculated with 1 l of preculture and incubated for 4 days at 21°, at an aeration rate of 0.5 l/1 l medium/minute, at 0.5 bar pressure and 150 rpm.
d) Second intermediate culture 500 l of intermediate culture medium in a 750 l steel fermenter are inoculated with 50 l of first intermediate culture.

Composition of the intermediate culture medium:

| malt extract, liquid | 50 g |
|---|---|
| yeast extract | 10 g |
| $FeSO_4.7H_2O$ | 16.68 mg |
| $ZnSO_4.7H_2O$ | 6.88 mg |
| demineralised water | ad 1000 ml | pH 5.6–5.8. Sterilisation: 20 minutes at 120°.

Incubation takes place for 3 days at 21° whilst stirring (100 rpm), at 0.5 bar pressure, with aeration (0.5/1 l medium/minute).
e) Main culture 3000 l of main culture medium in a 4500 l steel fermenter are inoculated with the second intermediate culture.

Composition of the main culture medium:

| malt extract, liquid | 40 g |
|---|---|
| yeast extract | 8 g |
| citric acid | 11.77 g |
| NaOH 1 N | 112 ml |
| HCl 1 N | 44 ml |
| demineralised water | ad 1000 ml |

Prior to sterilisation the pH value is adjusted to 3.8 to 4.1 with NaOH/HCL. Sterilisation: 20 minutes at 120°.

Incubation takes place for 5 days at 21° whilst stirring (50 rpm), at 0.5 bar pressure and with aeration (1.0 l/1 l medium/minute). Formation of foam is prevented using a silicone antifoaming agent.
f) Extraction 3400 l of fermentation broth are adjusted to pH 6 with dilute sulfuric acid and then separated using a Westfalia separator to yield 2500 l of culture liltrate and about 300 kg of mycelium. The culture filtrate is subsequently extracted twice in a Podbielniak counter-current extractor with twice 2500 l of ethyl acetate. The two organic extracts are combined and concentrated to 600 l in a Kühni gravity stream evaporator (heating temperature 75°, pressure 150 torr). This concentrate is then further concentrated to about 20 l in a B üchi circulatory evaporator with water ring vacuum pump, at a maximum concentrate temperature of 30° and is evaporated to dryness in the same way at a bath temperature of 50°. 485 g of crude extract are obtained. The 800 kg of mycelium are homogenised three times in a Dispax reactor, each time for 2 hours and using 800 l of 90% methanol. The bio-mass is centrifuged in a Westfalia separator. The three methanolic extracts are combined and the methanol is removed in a Büchi circulatory evaporator whilst adding water at a maximum concentrate temperature of 40°. The aqueous mycelium extract (3001l) is adjusted to a pH of 6.0 with dilute sulphuric acid and extracted thrice, each time with 400 l of ethyl acetate. After washing the extracts with 200 l of water they are combined and concentrated in a B üchi and Schmid circulatory evaporator. Concentration to dryness then follows as for the culture liltrate extract. 500 g of mycelium extract are obtained.

In order to remove antimicrobially inactive fats the crude extracts are separately dissolved in 10 times the amount of 90% methanol and are subsequently partitioned in 3 stages with hexane (in a ratio of 1:1). The combined methanolic phases are concentrated to about ⅓ of the volume whilst adding water and the aqueous concentrate is extracted thrice with the same volume of ethyl acetate. After evaporation in a Büchi rotary evaporator at 50° the combined organic extracts yield 201 g of culture filtrate extract and 221 g of mycelium extract, both of which show activity against yeast.
g) Isolation of the title compounds from the mycelium extract 220 g of scoured crude extract are introduced onto a column of 2.5 kg silicagel Merck 60 (grain size 0.04–0.063 mm, diameter 13 cm, height 50 cm). Elution takes place using methylene chloride as an eluant, with the methanol content increasing in stages. 500 ml per fraction are collected under a pressure of 2–3 bar. Analysis of the fractions by thin-layer chromatography is effected on silicagel Merck 60 plates, with methylene chloride/methanol (95:5) as the eluant and iodine as the detection reagent. The eluates with methylene chloride+1.5% methanol (fractions 30–48) are combined and after evaporation under reduced pressure yield 65 g of residue. After repeated crystallisation from methanol the first title compound is obtained pure.

Subsequent eluates with methylene chloride+2% methanol (fractions 95–111) yield 2.3 g of residue after evaporation. This mixed fraction is dissolved in 50 ml of methanol and introduced onto a column of 500 g of Sephadex $LH_{20}$ in methanol. Elution with methanol yields 1.1 g of fractions which contain the third title compound. Further separation of this material by chromatography on 150 g of silicagel H (column diameter 4.5 cm, height 28 cm) with methylene chloride+3% methanol as the eluant yields the crude product of the second title compound. Subsequent crystallisation from methanol yields that compound as a pure substance.

h) Isolation of the title compounds from the culture filtrate extract

The scoured crude extract (201 g) is separated by chromatography, analogously to the mycelium extract, on 2.5 kg of silicagel 60 Merck (grain size 0.040–0.063 mm). Elution is effected firstly with methylene chloride+1.5% methanol, then with methylene chloride+2% methanol and with a fraction size of 500 ml.

Fractions 37–50 obtained by elution with methylene chloride+2% methanol yield pure first title compound after evaporation and subsequent crystallisation of the residue from methanol. The subsequent eluates, fractions 51–64 with methylene chloride+2% methanol, yield upon evaporation 10 g of a mixed fraction which contains the second title compound together with impurities. More concentrated product is obtained after repeated medium-pressure chromatography on 1 kg of silicagel Merck 60 (grain size 0.040–0.063 vmm) and elution first with methylene chloride+2% methanol and then with methylene chloride+ 3% methanol. Crystallisation from methanol yields the pure second title compound.

Fractions 65–78 are combined and the evaporation residue (8.8 g) further purified by chromatography on 1 kg of silicagel Merck 60 (grain size 0.040–0.063 mm). Elution (100 ml per fraction) is effected with toluene/propanol-2/water 91.5:8:0.5, whereby the first eluates yield the second title compound as an amorphous preparation which is uniform on thin-layer chromatography after evaporation. The subsequent fractions are combined after analysis by thin-layer chromatography (eluant: methylene chloride/propanol-2 9:1 on silicagel Merck plates) and are subsequently evaporated to dryness. The 2.7 g residue is crystallised twice from diisopropylether to produce pure third title compound.

Characterization data:

| Title compound | M.P. | $[\alpha]_D 20$ |
|---|---|---|
| First | 236–238°1) | –228° c = 0.6 in chloroform |
| Second | 214–216°1) | –220° c = 0.5 in methanol |
| Third | 192–198°1) | –192° c = 0.5 in methanol |

1)colourless crystals, from methanol

NMR (first title compound): 4:1 mixture of conformers
Main component: 1.41 (d, J=7 Hz, H-10β), 2.50, 2.80, 2.91, 3.00, 3.45 (5x s, N—$CH_3$), 3.80 (s, $OCH_3$), 3.13 (d, 10 Hz, MeIle-αH), 3.46 (dd, $J_1$=3 Hz, $J_2$=17.5 Hz, H-7α'), 3.65 (d, br, J=14 Hz, H-Ie'), 4.05 (dd, $J_1$=5.5 Hz, $J_2$=17.5 Hz, H-7α), 4.29 (dd, br, $J_1$=11 Hz, $J_2$=14 Hz, H-1e'), 4.34 (d, J=10.5 Hz, MeVal-αH), 4.55 (t, J=10 Hz, H-3α, 4.76 (d, J=11Hz, MeVal-αH), 5.22 (dt, $J_1$=6 Hz, $J_2$=10 Hz, H-9α), 5.31 (d, J=11 Hz, MeIle-αH), 5.47 (q, J=7 Hz, H-10α), 5.67 (d, br, H-1α), 6.35 (dd, $J_1$=5.5 Hz, $J_2$=11.5 Hz, H-4α), Other component: 1.39 (d, J=7 Hz, H-10β), 2.61, 2.80, 2.90, 2.98, 2.99 (5x s, N-$CH_3$), 3.74 (s, $OCH_3$).
13C-NMR of main component: 40.9 (7αC), 43.2 (1eC), 46.4 (1αC), 51.0 (9αC), 52.0 (4αC), 54.6 (3αC), 55.2 ($OCH_3$), 56.5 (MeIle-αC, correlates with 5.31), 61.5 (MeVal-αC, correlates with 4.76), 66.8 (MeVal-αC, correlates with 4.34), 67.0 (10αC), 74.5 (MeIle-αC, correlates with 3.13).

Example 2:
Cyclo-[Pec-MeVal-Val-MeAsp(β-O-tert-butyl)-MeIle-MeIle-Gly-MeVal-Tyr(Me)-D-Lact]
[$R_1$, $R_2$, $R_3$, $R_5$, X, Y, $C_{10}$=as for 1st compound of Example 1; $R_4$=—COOtBu]
[process variant b); esterification]

To a solution of 4.5 g of the first title compound of Example 1 in 200 ml of boiling benzene are added dropwise 4.4 ml of dimethylformamide-di-tert-butylacetal. The solution is kept at boiling temperature until reaction is complete (about 4 hours, check by thin-layer chromatography). The solution is then allowed to cool, washed 5 times with water, the organic phase is dried over sodium sulfate. The oil obtained after evaporation of the solvent is purified by chromatography over silicagel using hexane/ethyl acetate 1:5 as an eluant. The title compound is obtained (colourless foam):

NMR: 3.5:1 mixture of conformers:
Main component: 2.70, 2.80, 2.91, 2.96, 3.04 ($NCH_3$), 3.76 ($OCH_3$), 1.31 (tBu).
Other component: 2.67, 2.79, 3.02, 3.04, 3.23 (N-$CH_3$), 3.80 ($OCH_3$), 1.36 (tBu).

The following compounds of formula I are obtained in a manner analogous to Example 2 starting from the corresponding compound wherein $R_4$ is carboxyl, i.e. from the first title compound of Example 1 or the title compound of Example 39 [$R_1$, $R_2$, $R_5$, X, Y, $C_{10}$=as for 1st compound of Example 1]:

| Example No. | $R_3$ | $R_4$ | Characterization data |
|---|---|---|---|
| 3 | p-MeO—Phe | —COOBz | colourless foam; NMR* |
| 4 | p-MeO—Phe | —COO($CH_2$)$_2$Si$Me_3$ | colourless foam; NMR* |
| 5 | p-MeO—Phe | —COO($CH_2$)$_7$Me | colourless powder; NMR* |
| 6 | p-OH—Phe | —COOtBu | colourless solid; NMR* |
| 7 | p-OH—Phe | —COOBz | colourless foam; NMR* |
| 8 | p-OH—Phe | —COO($CH_2$)$_2$Si$Me_3$ | colourless foam; NMR* |
| 9 | p-MeO—Phe | —COO($CH_2$)$_2$tBu | colourless foam; NMR* |
| 10 | p-MeO—Phe | —COO($CH_2$)$_2$iPr | colourless foam; NMR* |
| 11 | p-MeO—Phe | —COOCH($CH_3$)tBu | colourless solid; NMR* |
| 12** | p-tBuO—Phe | —COOtBu | colourless solid; NMR* |

**by reaction of the compound of Example 39 with $Me_2$NCH(OtBu)$_2$
*NMR:
Example 3: 1.3:1 mixture of conformers
Main component: 2.72, 2.78, 2.90, 2.95, 3.02 (N—$CH_3$), 3.75 ($OCH_3$), 4.98, 5.07 (COOC$H_2$$C_6$$H_5$), 7.2–7.4 (Ar).
Other component: 2.60, 2.77, 3.00, 3.04, 3.29 (N—$CH_3$), 3.80 ($OCH_3$), 5.04, 5.15 (COOC$H_2$$C_6$$H_5$), 7.2–7.4 (Ar).
Example 4: 1.5:1 mixture of conformers
Main component: 0.00 (Si($CH_3$)$_3$), 2.72, 2.79, 2.90, 2.92 3.07 (N—$CH_3$), 3.76 ($OCH_3$), 3.90 (COOC$H_2$—).
Other component: 0.01 (Si($CH_3$)$_3$), 2.64, 2.79, 2.99, 3.05, 3.33 (N—$CH_3$), 3.80 ($OCH_3$), 3.90 (COOC$H_2$—).
Example 5: 1.6:1 mixture of conformers
Main component: 2.73, 2.79, 2.90, 2.93, 3.05 (N—$CH_3$), 3.75 ($OCH_3$), 3.92 (COOC$H_2$—).

-continued

| Example No. | $R_3$ | $R_4$ | Characterization data |
|---|---|---|---|

Other component: 2.64, 2.79, 3.00, 3.03, 3.31 (N—$CH_3$), 3.80 ($OCH_3$), 3.92 ($COOH_2$—).
Example 6: 3:1 mixture of conformers
Main component: 2.72, 2.81, 2.85, 2.99, 3.04 (N—$CH_3$), $OCH_3$ is missing, 1.31 (tBu).
Other component: 2.57, 2.79, 2.96, 3.05, 3.34 (N—$CH_3$), $OCH_3$ is missing, 1.36 (tBu).
Example 7: 1.2:1 mixture of conformers
Main component: 2.69, 2.79, 2.82, 2.98, 3.06 (N—$CH_3$), $OCH_3$ is missing, 5.06, 5.10 ($COOCH_2$—), 7.20–7.40 (Ar).
Example 8: 2:1 mixture of conformers
Main component: 0.00 ($Si(CH_3)_3$), 2.52, 2.80, 2.83, 2.95, 3.06 (N—$CH_3$), $OCH_3$ is missing.
Other component: 0.01 ($Si(CH_3)_3$), 2.69, 2.84, 3.01, 3.04, 3.42 (N—$CH_3$), $OCH_3$ is missing.
Example 9: 1:1.3 mixture of conformers
0.88, 0.89 (tBu), 2.62, 2.72, 2.79, 2.79, 2.90, 2.92, 2.98, 3.03, 3.05, 3.34 (N—$CH_3$), 3.75, 3.80 ($OCH_3$).
Example 10: 1.5:1 mixture of conformers
Main component: 2.72, 2.78, 2.90, 2.92, 3.05 (N—$CH_3$), 3.75 ($OCH_3$).
Other component: 2.62, 2.78, 2.99, 3.03, 3.32 (N—$CH_3$), 3.80 ($OCH_3$).
Example 11: mixture of diastereoisomers and rotamers
2.64, 2.66, 2.69, 2.72 (s, N—$CH_3$); 4.465 (q, J=7Hz), 4.48 (q, J=7Hz), 0.91 (d, J=7Hz), 1.08 (d, J=7Hz).
Example 12: 4:1 mixture of conformers
Main component: 2.70, 2.79, 2.96, 2.96, 3.05 (N—$CH_3$).

The dimethylformamide acetals used for the reaction may be obtained by reaction of dimethylformamiddimethylacetal with an appropriate alcohol, as e.g. for:

dimethylformamid-bis-trimethylsilylacetal (B.P. 125°–127°/11 Torr);

dimethylformamid-bis-(3,3-dimethyl-1-butyl)acetal (B.P. 114°–115°/14 Torr);

dimethylformamid-bis-(3,3-dimethyl-2-butyl)acetal (B.P. 113°–114°/14 Torr);

dimethylformamid-diisopentylacetal (B.P. 114°–115°/14 Torr).

Example 13:
Cyclo-[Pec-MeVal-Val-MeAsp(β-O-allyl)-MeIle-MeIle-Gly-MeVal-Tyr(Me)-D-Lact]

[$R_1$, $R_2$, $R_3$, $R_5$, X, Y, $C_{10}$=as for 1st compound of Example 1; $R_4$=—COOallyl]

[process variant b); esterification]

560 mg of first title compound of Example 1 are heated for 3 hours at reflux temperature with 140 mg potassium carbonate and 0.42 ml of allyl bromide in 25 ml of acetone. This is followed by evaporation of the solvent, acidification with 0.1N HCl solution, triple extraction with ethyl acetate, washing of the organic solution thrice with saturated aqueous sodium chloride solution, drying over sodium sulfate, evaporation of the solvent and chromatography over silicagel using ethyl acetate as an eluant. The title compound is obtained (M.P. 132°–135°).

NMR:

1.3:1 mixture of conformers

Main component: 2.73, 2.78, 2.89, 2.92, 3.06 (N—$CH_3$), 3.75 ($OCH_3$), 4.47 ($COOCH_2$), 5.16, 5.21, 5.84 (—CH=$CH_2$).

Other component: 2.60, 2.78, 3.00, 3.04, 3.32 (N—$CH_3$), 3.80 ($OCH_3$), 4.47 ($COOCH_2$—), 5.16, 5.21, 5.84 (—CH=$CH_2$).

The following compounds of formula I are obtained in a manner analogous to Example 13, starting from the first title compound of Example 1 or, for Example 19, from the compound of Example 6 [$R_1$, $R_2$, $R_5$, X, Y, $C_{10}$=as for 1st compound of Example 1]:

| Example No. | $R_3$ | $R_4$ | Characterization data |
|---|---|---|---|
| 14[1] | p-MeO—Phe | —COOPhe | colourless resin; NMR* |
| 15[2] | p-MeO—Phe | —COOCH$_2$(1-adamantyl) | colourless foam; NMR* |
| 16 | p-MeO—Phe | —COO(1-adamantyl) | colourless solid; NMR* |
| 17 | p-MeO—Phe | —COO(2-adamantyl) | colourless solid; NMR* |
| 18 | p-MeO—Phe | —COO-bornyl | colourless solid; NMR* |
| 19[3] | p-OH—Phe | —COO-benzhydryl | M.P. 204–205° (methanol) |

[1] by reaction with chloromethylene-dimethylammonium chloride in the presence of pyridine and phenol at −20°
[2] by reaction with 2-chloro-1-methylpyridinium iodide and 1-adamantylmethanol in toluene in the presence of tripropylamine at reflux temperature
[3] by reaction with diphenyldiazomethane in methanol for 6 hours at 60°

*NMR:
Example 14: 1.5:1 mixture of conformers
Main component: 2.71, 2.73, 2.79, 2.83, 3.17 (N—$CH_3$), 3.75 ($OCH_3$), 7.1–7.3 (Ar).
Other component: 2.66, 2.83, 2.98, 3.15, 3.35 (N—$CH_3$), 3.81, ($OCH_3$), 7.1–7.3 (Ar).
Example 15: 1.5:1 mixture of conformers
Main component: 2.73, 2.79, 2.90, 2.95, 3.05 (N—$CH_3$), 3.75 ($OCH_3$).
Other component: 2.63, 2.78, 3.01, 3.02, 3.50 (N—$CH_3$), 3.79 ($OCH_3$).
Example 16: 3:1 mixture of conformers
Main component: 2.66, 2.78, 2.89, 2.95, 3.02 (N—$CH_3$), 3.75 ($OCH_3$).
Other component: 2.63, 2.78, 2.99, 3.01, 3.28 (N—$CH_3$), 3.79 ($OCH_3$).
Example 17: 5:3 mixture of conformers
Main component: 2.67, 2.79, 2.92, 2.93, 3.04 (N—$CH_3$), 3.75 ($OCH_3$).
Other component: 2.60, 2.78, 2.99, 3.01, 3.30 (N—$CH_3$), 3.79 ($OCH_3$).
Example 18: 3:1 mixture of conformers
Main component: 2.67, 2.80, 2.93, 2.96, 3.07 (N—$CH_3$), 3.76 ($OCH_3$).
Other component: 2.65, 2.79, 3.03, 3.05, 3.24 (N—$CH_3$), 3.80 ($OCH_3$).

The compounds of Examples 40 to 50, 52, 57 to 59, 64 to 69, 77 and 78 can also be obtained according to process b) (esterification) in a manner analogous to Example 2 or 13.

Example 20:
Cyclo-[Pec-MeVal-Val-MeAsp(β-allylamide)-MeIle-MeIle-Gly-MeVal-Tyr(Me)-D-Lact]

[$R_1$, $R_2$, $R_3$, $R_5$, X, Y, $C_{10}$=as for 1st compound of Example 1; $R_4$=—CONH—allyl]

[process variant c); amidation]

To a suspension of chloromethylene-dimethylammonium chloride (prepared from 2.56 ml of dimethylformamide and 0.96 ml of oxalyl chloride in 16 ml of acetonitrile) is added 2.25 g of first title compound of Example 1 in 25 ml of acetonitrtle and thereafter 0.27 ml of allylamine in 3 ml of pyridine is dropwise at −30°. After 20 hours at −20° the mixture is poured onto 0.2N aqueous sodium chloride solution and extracted thrice with ethyl acetate. The organic phase is washed thrice with water, dried over sodium sulfate and the solvent evaporated under reduced pressure. The crude title product is chromatographed over silicagel using ethyl acetate as an eluant. The title compound is obtained (colourless amorphous solid):

NMR:

1.2:1 mixture of conformers
2.67, 2.67, 2.77, 2.78, 2.83, 2.89, 3.01, 3.10, 3.30 (N—$CH_3$), 3.75, 3.80 ($OCH_3$), 5.00, 5.09, 5.71 (—CH=$CH_2$).

The following compounds of formula I are obtained in analogous manner [$R_1$, $R_2$, $R_3$, $R_5$, X, Y, $C_{10}$=as for 1st compound of Example 1]:

| Example No. | $R_4$ | Characterization data |
|---|---|---|
| 21 | —CONH$CH_2$(2-furyl) | colourless foam; NMR* |
| 22 | —CONH$CH_2$SiMe$_3$ | M.P. 173–175°; NMR* |
| 23 | —CONH-benzhydryl | colourless foam; NMR* |
| 24 | —CONH$CH_2$COOBz | colourless solid; NMR* |
| 25 | —CONH$CH_2$COOtBu | colourless foam; NMR* |
| 26 | —CONHC(iPr)COOBz<br>$\vdots$<br>H | colourless solid; NMR* |
| 27 | —CONHtBu | M.P. 161.5–164.5°; NMR* |
| 28 | —CONH-neopentyl | colourless solid;<br>M.P. 165–168°; NMR* |
| 29 | —CONHC(iPr)COOtBu<br>$\vdots$<br>H | colourless solid;<br>M.P. 155–157°; NMR* |
| 30 | —CONH-isopentyl | colourless foam; NMR* |
| 31 | —CO(piperidin-1-yl) | amorphous solid;<br>M.P. 159–161°; NMR* |
| 32 | —CONH(1-adamantyl) | colourless solid;<br>M.P. 228–229°; NMR* |
| 33 | —CON⟨(pyrrolidine ring)⟩<br>H  COOtBu | colourless solid;<br>M.P. 138–142°; NMR* |
| 34 | —CONHC(iPr)$CH_2$OSi(Me)$_2$tBu<br>$\vdots$<br>H | white crystals;<br>M.P. 144°; NMR* |
| 35 | —CON$Et_2$ | white crystals; M.P. 234–236°<br>$[\alpha]_D^{20} = -211°$ (MeOH) |
| 36 | —CONH(p-Br—Phe) | white crystals; M.P. 198–201°<br>$[\alpha]_D^{20} = -217°$ (CHCl$_3$) |
| 37 | —CONH(p-I—Phe) | M.P. 202–205°;<br>$[\alpha]_D^{20} = -179°$ (MeOH) |
| 38 | —CONH($CH_2$)$_3$NMe$_2$ | white crystals;<br>M.P. 190° (dec.)<br>(hydrochloride) |

*NMR:

Example 21: 1.1:1 mixture of conformers
2.63, 2.65, 2.78, 2.79, 2.84, 2.91, 2.98, 3.01, 3.10, 3.26(N—$CH_3$), 3.75, 3.80($OCH_3$), 6.10, 6.16, 6.25, 6.27, 7.24, 7.27(furyl).

Example 22: 1.2:1 mixture of conformers
0.00(Si($CH_3$)$_3$), 2.65, 2.66, 2.78, 2.79, 2.87, 2.92, 3.00, 3.06, 3.37(N—$CH_3$), 3.75, 3.79($OCH_3$).

Example 23: 2:1 mixture of conformers
Main component: 2.62, 2.74, 2.77, 2.99, 3.08(N—$CH_3$), 3.77($OCH_3$), 7.1–7.4(—$C_6H_5$).
Other component: 2.62, 2.77, 2.87, 2.89, 2.92(N—$CH_3$), 3.73($OCH_3$), 7.1–7.4(—$C_6H_5$).

Example 24: 1:1 mixture of conformers
2.55, 2.60, 2.78, 2.78, 2.84, 2.91, 2.96, 3.04, 3.10, 3.31(N—$CH_3$), 3.57, 3.78, 3.94, 4.05(—NH$CH_2$COO—), 3.75, 3.81($OCH_3$), 5.10 (COO$CH_2C_6H_5$), 7.2–7.4(—$C_6H_5$).

Example 25: 1:1 mixture of conformers
1.42(tBu), 2.56, 2.77, 2.79, 2.84, 2.90, 2.97, 3.03, 3.09, 3.37 (N—$CH_3$), 3.52, 3.80, 4.04, 4.11(—NH—$CH_2$—COO—), 3.75, 3.81($OCH_3$).

| Example No. | R$_4$ | Characterization data |
|---|---|---|

Example 26: 2:1 mixture of conformers
Main component: 2.43, 2.77, 2.96, 2.96, 3.48(N—CH$_3$), 3.81(OCH$_3$), 4.91, 5.03(COOCH$_2$C$_6$H$_5$), 7.2–7.4(—C$_6$H$_5$).
Other component: 2.56, 2.79, 2.89, 2.99, 3.07(N—CH$_3$), 3.75(OCH$_3$), 4.91, 5.03(COOCH$_2$C$_6$H$_5$), 7.2–7.4(—C$_6$H$_5$).
Example 27: 1:1 mixture of conformers
1.19, 1.23(tBu), 2.67, 2.67, 2.78, 2.79, 2.90, 2.97, 3.03, 3.06, 3.06, 3.40(N—CH$_3$), 3.76, 3.79(OCH$_3$).
Example 28: 1:1 mixture of conformers
0.80, 0.85(tBu), 1.42, 1.43(10-CH$_3$), 2.64, 2.67, 2.77, 1.78, 2.88, 2.92, 2.94, 3.04, 3.06, 3.38(N—CH$_3$) 3.75, 3.78(OCH$_3$).
Example 29: 14:11 mixture of conformers
Main component: 1.36(tBu), 2.45, 2.78, 2.96, 2.97, 3.51(N—CH$_3$), 3.76(OCH$_3$).
Other component: 1.46(tBu), 2.57, 2.79, 2.88, 3.02, 3.07(N—CH$_3$), 3.81(OCH$_3$).
Example 30: 7:6 mixture of conformers
Main component: 2.68, 2.78, 2.89, 3.08, 3.35(N—CH$_3$), 3.74(OCH$_3$).
Other component: 2.65, 2.77, 2.83, 3.00, 3.03(N—CH$_3$), 3.79(OCH$_3$).
Example 31: 8:1 mixture of conformers
Main component: 2.64, 2.80, 2.96, 3.01, 3.10(N—CH$_3$), 3.77(OCH$_3$).
Other component: 2.55, 2.77, 3.05, 3.08, 3.23(N—CH$_3$), 3.81(OCH$_3$).
Example 32: 3:2 mixture of conformers
Main component: 2.66, 2.78, 2.88, 2.96, 3.05(N—CH$_3$), 3.75(OCH$_3$).
Other component: 2.67, 2.77, 3.02, 3.05, 3.40(N—CH$_3$), 3.78(OCH$_3$).
Example 33: mixture of rotation isomers at room temperature, single component at 403° K. in DMSO-d$_6$:
1.40(tBu), 2.65, 2.73, 2.88, 2.99(N—CH$_3$), 3.73(OCH$_3$).
Example 34: 1.5:1 mixture of conformers
Main component: 0.89(tBu), 2.60, 2.77, 2.78, 3.00, 3.08(N—CH$_3$), 3.75(OCH$_3$).
Other component: 0.86(tBu), 2.63, 2.87, 3.01, 3.04, 3.37(N—CH$_3$), 3.77(OCH$_3$).

The compounds of Examples 53 to 56, 60 to 63, 82 and 83 can also be obtained according to process c) (amidation) in a manner analogous to Example 20.

Example 39:
Cyclo-[Pec-MeVal-Val-MeAsp-MeIle-MeIle-Gly-MeVal-Tyr-D-Lact]
[R$_1$, R$_2$, R$_5$, X, Y, C$_{10}$=as for 1st compound of Example 1; R$_3$=p—OH—Phe; R$_4$=—COOH]
[process variant d); ether splitting]

A solution of aluminium iodide is freshly prepared by heating to boiling for 3.5 hours 2.5 g of aluminium foil and 19 g iodine in 100 ml of carbon disulfide, 5.6 g of first title compound of Example 1 are added thereto at room temperature and the mixture is heated under reflux for 3 hours. The ice-cold solution is then added to ice-cold ammonium chloride solution and extracted thrice with ethyl acetate. The organic phases are washed with sodium thiosulfate solution and water and dried over sodium sulfate. After the solvent has been distilled off under reduced pressure the crude product is chromatographed over silicagel using dichloromethane/diisopropylether/methanol 10:4:1 as an eluent. The title compound is obtained (colourless foam; M.P. 217°–219°; [α]$_D^{20}$=–228° MeOH);
NMR:
6:1 mixture of conformers
Main component: 2.42, 2.79, 2.91, 3.00, 3.52 (N—CH$_3$), OCH$_3$ is missing, 3.80 (7-αH, 7-α'H), 6.65, 6.94 (Ar).
The compounds of Examples 7 and 8 can also be obtained according to process d) (ether splitting) in a manner analogous to Example 39.

Example 40:
Cyclo-[Pec-MeVal-Val-MeAsp(β-O-tert-butyl)-MeIle-MeIle-Gly-MeVal-Tyr(allyl)-D-Lact]
[R$_1$, R$_2$, R$_5$, X, Y, C$_{10}$=as for 1st compound of Example 1; R$_3$=p-allyloxy—Phe; R$_4$=—COOtBu]
[process variant e); introduction of R$_6'$]

58 mg of compound of Example 6 are heated for 4 hours at boiling temperature with 14 mg potassium carbonate and 0.042 ml of allyl bromide in 3 ml of acetone. After cooling off the solvent is evaporated under reduced pressure, the residue taken up in 0.1N hydrochloric acid and extracted thrice with ethyl acetate. The combined organic phases are washed thrice with saturated sodium chloride solution, dried over sodium sulfate and the solvent is distilled off. The residue is chromatographed over silicagel using hexane/ethyl acetate 1:5 as an eluent. The title compound is obtained (colourless foam):
NMR:
2.6:1 mixture of conformers
Main component: 1.31 (tBu), 2.70, 2.79, 2.91, 2.96, 3.04 (N—CH$_3$), 5.27, 5.41, 6.05 (—CH=CH$_2$).
Other component: 1.36 (tBu), 2.70, 2.78, 3.02, 3.05, 3.22 (N—CH$_3$), 5.27, 5.41, 6.05 (—CH=CH$_2$).

The following compounds of formula I are obtained in a manner analogous to Example 40 starting from the corresponding compound wherein R$_3$ is p—OH—Phe
[R$_1$, R$_2$, R$_5$, X, Y, C$_{10}$=as for 1st compound of Example 1]:

| Example No. | R₃ | R₄ | Characterization data |
|---|---|---|---|
| 41[1)] | p-(allyloxy)-Phe | —COOBz | amorphous solid; M.P. 113–116°; NMR* |
| 42[2)] | p-(allyloxy)-Phe | —COO(CH₂)₂SiMe₃ | colourless foam; NMR* |
| 43[3)] | p-(allyloxy)-Phe | —COOallyl | colourless foam; NMR* |
| 44[1)] | p-[BzOC(=O)CH₂O]—Phe | —COOBz | colourless solid; NMR* |
| 45[2)] | p-[BzOC(=O)CH₂O]—Phe | —COO(CH₂)₂SiMe₃ | colourless solid; NMR* |
| 46[2)] | p-BzO—Phe | —COO(CH₂)₂SiMe₃ | colourless solid; NMR* M.P. 127–130° |
| 47[2)] | p-(4-Br—BzO)—Phe | —COO(CH₂)₂SiMe₃ | colourless foam; NMR* |
| 48[2)] | p-(4-Cl—BzO)—Phe | —COO(CH₂)₂SiMe₃ | colourless solid; NMR* |
| 49[2)4)] | p-[(E)-3,7-dimethyl-2,6-octadien-1-yloxy-]-Phe | —COO(CH₂)₂SiMe₃ | colourless foam; NMR* |
| 50[5)] | p-[EtOC(=O)O]—Phe | —COO(CH₂)₂SiMe₃ | colourless amorphous powder; NMR* |
| 51[6)] | p-(acetoxy)-Phe | —COOH | M.P. 202–205° |

[1)] Starting from the compound of Example 7 or [2)] of Example 8
[3)] Starting from the compound of Example 39 and using two equivalents of allyl bromide
[4)] Using geranyl bromide in 1,2-dichloroethane and 0.1 N sodium hydroxide, with addition of a spoontip of tetrabutylammonium hydrogen sulfate and heating for 48 hours at reflux temperature
[5)] From 242 mg of compound of Example 8, using 0.029 ml of chloroformic acid ethyl ester, 10 ml of dichloromethane and 4 ml of 0.1 N sodium hydroxide, under addition of a spoontip of tetrabutylammonium hydrogen sulfate, stirring for 1 hour at room temperature
[6)] Starting from the compound of Example 39 and using acetic anhydride in pyridine, 24 hours at room temperature

*NMR:
Example 41: 1.3:1 mixture of conformers
Main component: 2.73, 2.78, 2.90, 2.94, 3.06 (N—CH₃), 4.98, 5.07 (COOCH₂C₆H₅), 5.27, 5.41, 6.05 (—CH=CH₂), 7.2–7.4 (Ar).
Other component: 2.64, 2.77, 3.01, 3.04, 3.28 (N—CH₃), 5.03, 5.15 (COOCH₂C₆H₅), 5.27, 5.46, 6.05 (—CH=CH₂), 7.2–7.4 (Ar).
Example 42: 1.5:1 mixture of conformers
Main component: 0.0 (Si(CH₃)₃), 2.73, 2.79, 2.91, 2.91, 3.02 (N—CH₃), 4.10 (COOCH₂—), 4.48 (OCH₂—), 5.27, 5.41, 6.05 (—CH=CH₂).
Other component: 0.01 (Si(CH₃)₃), 2.67, 2.79, 3.00, 3.05, 3.33 (N—CH₃), 4.10 (COOCH₂—), 4.53 (OCH₂—), 5.27, 5.46, 6.05 (—CH=CH₂).
Example 43: 1.2:1 mixture of conformers
Main component: 2.73, 2.79, 2.90, 2.92, 3.06 (N—CH₃), 4.47 (COOCH₂—), 4.53 (OCH₂—), 5.16, 5.21, 5.84 (—CH=CH₂), 5.27, 5.40, 6.04 (—CH=CH₂).
Other component: 2.64, 2.78, 3.00, 3.04, 3.31 (N—CH₃), 4.47 (COOCH₂—), 4.53 (OCH₂—), 5.16, 5.21, 5.84 (—CH=CH₂), 5.27, 5.47, 6.04 (—CH=CH₂).
Example 44: 1.3:1 mixture of conformers
Main component: 2.73, 2.78, 2.87, 2.94, 3.06 (N—CH₃), 4.65 (OCH₂CO), 4.98, 5.07 (COOCH₂C₆H₅), 5.25 (COOCH₂C₆H₅), 7.2–7.4 (Ar).
Other component: 2.65, 2.77, 2.98, 3.04, 3.28 (N—CH₃), 4.70 (OCH₂CO), 5.03, 5.15 (COOCH₂C₆H₅), 5.25 (COOCH₂C₆H₅), 7.2–7.4 (Ar).
Example 45: 1.5:1 mixture of conformers
Main component: 0.00 (Si(CH₃)₃), 2.72, 2.79, 2.82, 2.91, 3.06 (N—CH₃), 4.10 (COOCH₂—), 4.65 (OCH₂CO), 5.14, 7.36 (COOCH₂C₆H₅).
Other component: 0.01 (Si(CH₃)₃), 2.64, 2.79, 2.91, 2.93, 3.07 (N—CH₃), 4.10 (COOCH₂—), 4.70 (OCH₂CO), 5.16, 7.36 (COOCH₂C₆H₅).
Example 46: 1.5:1 mixture of conformers
Main component: 0.00 (Si(CH₃)₃), 2.64, 2.79, 2.91, 2.93, 3.07 (N—CH₃), 4.10 (COOCH₂—), 5.03 (OCH₂—) 7.3–7.5 (Ar).
Other component: 0.01 (Si(CH₃)₃), 2.63, 2.78, 3.00, 3.06, 3.34 (N—CH₃), 4.10 (COOCH₂—), 5.10 (OCH₂—), 7.3–7.5 (Ar).
Example 47: 1.1:1 mixture of conformers
Main component: 0.00 (Si(CH₃)₃), 2.64, 2.78, 2.89, 2.90, 3.05 (N—CH₃), 4.10 (COOCH₂—), 4.96 (OCH₂—), 7.33, 7.52 (Ar).
Other component: 0.01 (Si(CH₃)₃), 2.60, 2.78, 2.95, 3.04, 3.34 (N—CH₃), 4.10 (COOCH₂—), 5.04 (OCH₂—), 7.42, 7.50 (Ar).
Example 48: 1.2:1 mixture of conformers
Main component: 0.00 (Si(CH₃)₃), 2.65, 2.79, 2.90, 2.91, 3.06 (N—CH₃), 4.10 (COOCH₂—), 4.98 (OCH₂), 7.3–7.5 (Ar).
Other component: 0.01 (Si(CH₃)₃), 2.61, 2.78, 2.96, 3.05, 3.34 (N—CH₃), 4.10 (COOCH₂—), 5.06 (OCH₂—), 7.3–7.5 (Ar).
Example 49: 1.5:1 mixture of conformers
Main component: 0.00 (Si(CH₃)₃), 1.62, 1.69 (C=C(CH₃)₂), 2.75, 2.80, 2.90, 2.93, 3.07 (N—CH₃), 4.10 (COOCH₂—), 4.47 (O—CH₂—C=C).
Other component: 0.01 (Si(CH₃)₃), 1.62, 1.69 (C=C(CH₃)₂), 2.69, 2.79, 3.00, 3.05, 3.32 (N—CH₃), 4.10 (COOCH₂—), 4.13 (O—CH₂—C=C).
Example 50: 1.5:1 mixture of conformers
Main component: 0.00 (Si(CH₃)₃), 1.39 (OCOOCH₂CH₃), 2.57, 2.80, 2.89, 2.95, 3.07 (N—CH₃), 4.10 (COOCH₂—), 4.31 (OCOOCH₂CH₃).
Other component: 0.01 (Si(CH₃)₃), 1.40 (OCOOCH₂CH₃), 2.70, 2.80, 3.03, 3.05, 3.33 (N—CH₃), 4.10 (COOCH₂—), 4.31 (OCOOCH₂CH₃).

The compounds of Examples 1 to 5, 9 to 18, 20 to 38, 52 to and 69 to 83 can also be obtained according to process e) (introduction of R₆') in a manner analogous to Example 40.

Example 52:
Cyclo-[Pec-MeVal-Val-MeAsp(β-O-tert-butyl)-MeIle-MeIle-Gly-MeVal-Tyr(Me)-L-Lact][R₁, R₂, R₃, R₅, X, Y=as for 1st compound of Example 1; R$_4$=—COOtBu; C$_{10}$ has L-configuration]
process variant f); ring closure]

To a solution of 6.0 g H-D-Lact-Pec-MeVal-Val-MeAsp(β-O-tert-butyl)-MeIle-MeIle-Gly-MeVal-Tyr(Me)-OH and 4.8 g triphenylphosphin in 750 ml of dry toluene is added a solution of 2.37 ml of azodicarboxylic acid diethyl ester in 500 ml of dry toluene under stirring, dropwise and over 20 hours. After two days the solvent is distilled off under reduced pressure and the residue is separated from the triphenylphosphine oxide produced, by chromatography over Silicagel LH20 using dichloroethane as an eluant. The resultant crude product is purified by chromatography over silicagel using hexane/ethyl acetate 1:5 as an eluant. The title compound is obtained [colourless foam; M.P. 146°–148°; [α]$_D^{20}$=–221° (c=1.0, CH$_2$Cl$_2$)];
NMR:
5:1 mixture of conformers
Main component: 1.33 (tBu), 2.75, 2.76, 2.90, 3.04, 3.08 (N—CH$_3$), 3.76 (OCH$_3$).

The starting material (a compound of formula II) is obtained as follows:

16.2 g title compound of Example 2 are dissolved in 700 ml of a mixture of tetrahydrofuran/water 1:1 and 1.15 g lithium hydroxide monohydrate is added under stirring in small portions. After 17 hours the solution is acidified to pH 3 with 1N hydrochloric acid solution, the mixture is diluted with ethyl acetate and water and the organic phase discarded. The aqueous phase is extracted 4 times more with ethyl acetate. The combined organic phases are washed once with water and twice with saturated sodium chloride solution, dried over sodium sulfate and the solvent is removed under reduced pressure. H-D-Lact-Pec-MeVal-Val-MeAsp(β-O-tert-butyl)-MeIle-MeIle-Gly-MeVal-Tyr(Me)-OH is obtained (colourless solid).

The following compounds of formula I are obtained in a manner analogous to Example 52, starting from the corresponding compound of formula II [R$_1$, R$_2$, R$_3$, R$_5$, Y=as for 1st compound of Example 1; C$_{10}$ has the L-configuration]:

| Example No. | X | R$_4$ | Characterization data |
| --- | --- | --- | --- |
| 53[1] | O | —CONH-tBu | colourless solid; M.P. 160–162.5°; NMR* |
| 54[2] | O | —CONH-neopentyl | colourless solid; M.P. 164–166°; NMR* |
| 55[3] | O | —CONH—C(iPr)COOtBu<br>　　　　　｜<br>　　　　　H | colourless solid; M.P. 185–186°; NMR* |
| 56[4] | O | —CONH—CH$_2$SiMe$_3$ | colourless foam; NMR* |
| 57[5] | O | —COO(CH$_2$)$_2$tBu | colourless solid; NMR* |
| 58[6] | O | —COOCH(Me)tBu | colourless solid; NMR* |
| 59[7] | O | —COOCH$_2$(1-adamantyl) | colourless solid; NMR* |
| 60[8] | O | —CO(piperidin-1-yl) | colourless solid; NMR* |
| 61[9] | O | —CONH-(1-adamantyl) | colourless solid; M.P. 184–185°; NMR* |
| 62[10] | O | —CONH-isopentyl | colourless solid; NMR* |
| 63[11] | O | —CONH—C(iPr)CH$_2$OSi(Me$_2$)tBu<br>　　　　　｜<br>　　　　　H | colourless solid; M.P. 143–145°; NMR* |

*NMR:
Example 53: 2.5:1 mixture of conformers
Main component: 1.22(tBu), 1.39(1O—CH$_3$), 2.71, 2.75, 2.94, 3.03, 3.04(N—CH$_3$), 3.75(OCH$_3$).
Other component: 1.26(tBu), 1.43(1O—CH$_3$), 2.58, 2.74, 3.03, 3.07, 3.26(N—CH$_3$), 3.79(OCH$_3$).
Example 54: 2:1 mixture of conformers
Main component: 0.82(tBu), 1.39(1O—CH$_3$), 2.65, 2.76, 2.92, 3.00, 3.05(N—CH$_3$), 3.74(OCH$_3$).
Other component: 0.86(tBu), 1.44(1O—CH$_3$), 2.55, 2.75, 3.03, 3.05, 3.28(N—CH$_3$), 3.79(OCH$_3$).
Example 55: 1.2:1 mixture of conformers
1.37, 1.45(tBu), 2.40, 2.62, 2.76, 2.76, 2.95, 2.98, 3.02, 3.02, 3.06, 3.45(N—CH$_3$), 3.75, 3.80(OCH$_3$).
Example 56: 2:1 mixture of conformers
Main component: 0.01(Si(CH$_3$)$_3$), 1.40(1O—CH$_3$), 2.67, 2.76, 2.90, 2.99, 3.06(N—CH$_3$), 3.74(OCH$_3$).
Other component: 0.03(Si(CH$_3$)$_3$), 1.44(1O—CH$_3$), 2.56, 2.75, 3.02, 3.05, 3.31(N—CH$_3$), 3.80(OCH$_3$).
Example 57: mixture of conformers
3.705, 3.750, 3.785, 3.800(s, OCH$_3$).
Example 58: mixture of conformers
3.755, 3.760, 3.80(s, OCH$_3$); 4.425(q, J=7HZ), 4.450(q, J=7Hz)
Example 59: 3:1 mixture of conformers
Main component: 2.75, 2.78, 2.87, 3.06, 3.09(N—CH$_3$), 3.76(OCH$_3$).
Example 60: 3:1 mixture of conformers
Main component: 2.69, 2.75, 2.95, 3.08, 3.09(N—CH$_3$), 3.76(OCH$_3$).
Other component: 2.54, 2.73, 3.05, 3.13, 3.18(N—CH$_3$), 3.81(OCH$_3$).
Example 61: 4:1 mixture of conformers
Main component: 2.67, 2.75, 2.95, 3.01, 3.05(N—CH$_3$), 3.75(OCH$_3$).

| Example No. | X | R₄ | Characterization data |
|---|---|---|---|
| | | | Other component: 2.58, 2.75, 3.04, 3.07, 3.28(N—CH₃), 3.79(OCH₃).<br>Example 62: 2:1 mixture of conformers<br>Main component: 2.64, 2.76, 2.90, 2.96, 3.07(N—CH₃), 3.74(OCH₃).<br>Other component: 2.55, 2.75, 3.00, 3.05, 3.31(N—CH₃), 3.79(OCH₃).<br>Example 63: 3:1 mixture of conformers<br>Main component: 2.67, 2.75, 2.95, 3.03, 3.08(N—CH₃), 3.75(OCH₃).<br>Other component: 2.56, 2.75, 3.04, 3.07, 3.29(N—CH₃), 3.78(OCH₃). |

[1] The corresponding starting material of formula II is prepared from the compound of Example 27
[2] The corresponding starting material of formula II is prepared from the compound of Example 28
[3] The corresponding starting material of formula II is prepared from the compound of Example 29
[4] The corresponding starting material of formula II is prepared from the compound of Example 22
[5] The corresponding starting material of formula II is prepared from the compound of Example 9
[6] The corresponding starting material of formula II is prepared from the compound of Example 11
[7] The corresponding starting material of formula II is prepared from the compound of Example 15
[8] The corresponding starting material of formula II is prepared from the compound of Example 31
[9] The corresponding starting material of formula II is prepared from the compound of Example 32
[10] The corresponding starting material of formula II is prepared from the compound of Example 30
[11] The corresponding starting material of formula II is prepared from the compound of Example 34

Example 64:
Cyclo-[Pec-MeVal-Val-MeAsp(β-O-tert-butyl)-MeIle-MeIle-Gly-MeVal-Tyr(Me)-Ala]
[$R_1$, $R_2$, $R_3$, $R_5$, Y=as for 1st compound of Example 1; $R_4$=—COOtBu; X=NH; $C_{10}$ has L-configuration]
process variant f); ring closure]

To a solution of 500 mg H-Ala-Pec-MeVal-Val-MeAsp(β-O-tert-butyl)-MeIle-MeIle-Gly-MeVal-Tyr(Me)-OH in 1.5 l of dichloromethane are added under energetic stirring 156 mg pentafluorophenol and 176 mg dicyclohexylcarbodiimide. After 2 days at room temperature the solution is concentrated to a volume of 150 ml and then washed successively with 0.2N sodium hydroxide, water and saturated sodium chloride solution, dried over sodium sulfate and the remaining solvent evaporated under reduced pressure. The residue is digested with diethylether, filtered and washed twice with diethylether. The ether solution is evaporated to dryness and the resultant solid chromatographed over silicagel, using ethyl acetate as an eluant. The title compound is obtained (colourless solid):
NMR:
Main component: 1.32 (tBu), 2.64, 2.77, 2.92, 2.97, 3.12 (N—CH₃), 3.79 (OCH₃).

The starting material (a compound of formula II) is obtained as follows:

a) H-D-Lact-Pec-MeVal-Val-MeAsp(β-O-tert-butyl)-MeIle-MeIle-Gly-MeVal-Tyr(Me)-O-benzyl 5.3 g H-D-Lact-Pec-MeVal-Val-MeAsp(β-O-tert-butyl)-MeIle-MeIle-Gly-MeVal-Tyr(Me)-OH (starting material for Example 52) are reacted with dimethylformamide dibenzylacetal analogously to Example 2. The crude product is purified by chromatography over silicagel using hexane/ethyl acetate 1:5 as an eluant. The product is a colourless foam.

b) H-D-Lact-(0-methanesulfonyl)-Pec-MeVal-Val-MeAsp(β-O-O-tert-butyl)-MeIle-MeIle-Gly-MeVal-Tyr(Me)-O-benzyl 4.5 g product of step a) above are dissolved in 35 ml of pyridine, cooled to 0° and reacted with 0.56 ml of methanesulfonic acid chloride added dropwise. After 3.5 hours at 0° the pyridine is removed under reduced pressure, the residue extracted with ethyl acetate and water. The organic phase is washed successively with 1N hydrochloric acid, 2% sodium hydrogen carbonate solution and saturated sodium chloride solution, dried over sodium sulfate, and the solvent is evaporated under reduced pressure. The resultant residue is washed with diethylether and filtered, and a solid product is obtained.

c) L-2-Azidopropion71-Pec-MeVal-Val-MeAsp(β-O-tert-butyl)-MeIle-MeIle-Gly-MeVal-Tyr(Me)-O-benzyl 1.24 g sodium azide is added to a solution of 5.3 g product of step b) above in 55 ml of dimethylformamide and the reaction mixture is stirred for 6 hours at 60°. After cooling to room temperature the mixture is diluted with ethyl acetate, washed 5 times with water and once with saturated sodium chloride solution, dried over sodium sulfate, and the solvent is removed under reduced pressure. The residue is chromatographed over silicagel using dichloromethane/ethyl acetate 1:2 to 1:5 as an eluant. The product is a colourless resin (IR: 2120 $cm^{-1}$).

d) H-Ala-Pec-MeVal-Val-MeAsp(β-O-tert-butyl)-MeIle-MeIle-Gly-MeVal-Tyr(Me)-OH 1.2 g product of step c) above is dissolved in 50 ml of ethanol and hydrogenated for 2.5 hours at normal pressure in a hydrogen atmosphere using 10% palladium over charcoal as an catalyst. The product obtained after removal of the catalyst by filtration and solvent evaporation under reduced pressure is a solid.

Example 65:
Cyclo-[Pec-MeVal-Val-MeAsp(β-O-tert-butyl)-MeIle-MeIle-Gly-MeVal-Tyr(Me)-D-Ala]
[$R_1$, $R_2$, $R_3$, $R_5$, Y=as for 1st compound of Example 1; $R_4$=—COOtBu; X=NH; $C_{10}$ has D-configuration]
[process variant f); ring closure]

H-D-Ala-Pec-MeVal-Val-MeAsp(B-O-tert-butyl)-MeIle-MeIle-Gly-MeVal-Tyr(Me)-OH is cyclized in a manner analogous to Example 64. The title compound is obtained as colourless foam:
NMR:
2.5:1 mixture of conformers Main component: 1.32 (tBu), 2.79, 2.80, 2.88, 2.96, 3.06 (N—CH$_3$), 3.76 (OCH$_3$).

The starting material (a compound of formula II) is obtained as follows:

a) H-L-Lact-{0-toluol-4-sulfonyl)-Pec-MeVal-Val-MeAsp (β-O-tert-butyl)-MeIle-MeIle-Gly-MeVal-Tyr(Me)-O-benzyl To a solution of 3 g product of step b) under Example 64 in 50 ml of dry toluence is added with stirring 1.22 g triphenylphosphine, 1.18 g zinc tosylate and 0.78 ml of azidodicarboxylic acid diethyl ester. After 2 hours a further 1.22 g triphenylphosphine and 0.78 ml of ester is added. After 3 days at room temperature the solvent is removed under reduced pressure and the residue is chromatographed over silicagel using hexane/ethyl acetate 1:2 to 1:5 as an eluant. The product is a colourless foam.

b) D-2-Azidopropionyl-Pec-MeVal-Val-MeAsp(β-O-tert-butyl)-MeIle-MeIle-Gly-MeVal-Tyr(Me)-O-benzyl The product of step a) above is reacted with sodium azide analogously to step c) under Example 64, The product is a colourless foam (IR: 2120 cm$^{-1}$).

c) H-D-Ala-Pec-MeVal-Val-MeAsp(β-O-tert-butyl)-MeIle-MeIle-Gly-MeVal-Tyr(Me)-OH

The product of step b) above is hydrogenated analogously to step d) under Example 64. The product is a colourless foam.

Example 66:
Cyclo-[Pec-MeVal-Val-MeAsp(β-O-tert-butyl)-MeIle-MeIle-Gly-MeVal-Tyr(Me)-D-Ala-Ala]
[R$_1$, R$_2$, R$_3$, R$_5$=as for 1st compound of Example 1; R$_4$=—COOtBu; X=NH; Y=L-Ala; C$_{10}$ has D-configuration]
[process variant f); ring closure]

H-D-Ala-Ala-Pec-MeVal-Val-MeAsp(β-O-tert-butyl)-MeIle-MeIle-Gly-MeVal-Tyr(Me)-OH is cyclised in a manner analogous to Example 64. The title compound is obtained (colourless foam);
NMR:
Main component: 1.23 (CH$_3$(Ala)), 1.33 (tBu), 2.72, 2.86, 2.88, 3.10, 3.20 (N—CH$_3$), 3.76 (OCH$_3$), 4.60, 4.95 (α-H(Ala)).

The starting material (a compound of formula II) is obtained as follows:

a) 4-Nitrobenzyloxycarbonyl-D-Ala-Ala-Pec-MeVal-Val-MeAsp-(β-O-tert-butyl)-MeIle-MeIle-Gly-MeVal-Tyr(Me)-OH To a solution of 2.6 g H-Ala-Pec-MeVal-Val-MeAsp(β-O-tert-butyl)-MeIle-MeIle-Gly-MeVal-Tyr(Me)-OH [see step d) under Example 64] in 20 ml of dimethylformamide are added 0.28 ml of triethylamine and 779 ml 4-nitrobenzyloxycarbonyl-D-alanyl-4-nitrophenylester and the reaction mixture is stirred for 4 days. The mixture is then diluted with ethyl acetate and agitated with 0.02N hydrochloric acid. The organic phase is washed 5 times with water and once with saturated sodium chloride solution, dried over sodium sulfate, and the solvent is evaporated under reduced pressure. The residue is chromatographed over silicagel using dichloromethane/methanol 9:1 to 4:1 as an eluant. The product is a colourless foam.

b) H-D-Ala-Ala-Pec-MeVal-Val-MeAsp-(B-0-tert-butyl)-MeIle-MeIle-Gly-MeVal-Tyr(me)-OH The product of step a) above is hydrogenated analogously to Example 64, step d). The product is colourless (M.P. 182°).

Example 67:
Cyclo-[Pec-MeVal-Val-MeAsp(β-O-tert-butyl)-MeIle-MeIle-Gly-MeVal-Tyr(Me)-D-Ala-D-Ala]
[R$_1$, R$_2$, R$_3$, R$_4$, R$_5$, X=as for Example 66; Y=D-Ala, C$_{10}$ has D-configuration]
[process variant f); ring closure]

H-D-Ala-D-Ala-Pec-MeVal-Val-MeAsp(β-O-tert-butyl)-MeIle-MeIle-Gly-MeVal-Tyr(Me)-OH is cyclised in a manner analogous to Example 64. The title compound is obtained (colourless foam):
NMR:
Main component: 1.34 (tBu), 2.78, 2.85, 2.92, 3.01, 3.15 (N—CH$_3$), 3.78 (OCH$_3$).

The starting material (a compound of formula II) is obtained as follows:

a) 4-NitrobenzyloxTcarbonyl-D-Ala-D-Ala-Pec-MeVal-Val-MeAsp(β-O-tert-butyl)-MeIle-MeIle-Gly-MeVal-Tyr (Me)-OH H-D-Ala-Pec-MeVal-Val-MeAsp(β-O-tert-butyl)-MeIle-MeIle-Gly-MeVal-Tyr(Me)-OH [see step c) under Example 65] is reacted analogously to Example 64, step a). The product is a colourless foam.

b) H-D-Ala-D-Ala-Pec-MeVal-Val-MeAsp(β-O-tert-butyl)-MeIle-MeIle-Gly-MeVal-Tyr(Me)-OH The product of step a) above is hydrogenated analogously to Example 64, step d). The product is a colourless foam.

Example 68:
Cyclo-[Pec-MeVal-Val-MeAsp(β-O-tert-butyl)-MeIle-MeIle-Gly-MeVal-Tyr-L-Lact]
[R$_1$, R$_2$, R$_5$, X, Y=as for 1st compound of Example 1; R$_3$=p-OH-Phe; R$_4$=—COOtBu; C$_{10}$ has L-configuration]
[process variant f); ring closure followed by deprotection]

H-D-Lact-Pec-MeVal-Val-MeAsp(β-O-tert-butyl)-MeIle-MeIle-Gly-MeVal-Tyr(tert-butyldimethylsilyl)-OH is reacted analogously to Example 52. The compound obtained, cyclo-[Pec-MeVal-Val-MeAsp(β-O-tert-butyl)-MeIle-MeIle-Gly-MeVal-Tyr(tert-butyl-dimethylsilyl)-L-Lact] (colourless foam) is deprotected analogously to Example 83. The title compound is obtained (colourless solid):
NMR:
6:1 mixture of conformers
Main component: 1.23 (d, J=7 Hz, 10-Hβ), 1.34 (tBu), 2.76, 2.85, 2.96, 2.97, 2.99 (N—CH$_3$), 5.57 (q, J=7 Hz, 10-Hα), 6.23 (dd, J$_1$=4 Hz, J$_2$=10 Hz, 4-Hα).

The starting material (a compound of formula II) is obtained as follows:

a) Cyclo-[Pec-MeVal-Val-MeAsp(β-O-tert-butyl)-MeIle-MeIle-Gly-MeVal-Tyr(tert-butyl-dimethylsilyl)-D-Lact]

To a solution of Cyclo-[Pec-MeVal-Val-MeAsp(β-O-tert-butyl)-MeIle-MeIle-Gly-MeVal-Tyr-D-Lact] and 0.534 g imidazol in 50 ml of dry dimethylformamide is added under stirring 1.15 g tert-butyldimethylchlorosilane and the reaction mixture is stirred for 5 hours at 80°. After cooling to room temperature the solution is poured onto ice-water and the precipitate filtered off. The precipitate is washed with water, dried and treated with petroleum ether. The product obtained is a colourless solid.

b) H-D-Lact-Pec-MeVal-Val-MeAsp(β-O-tert-butyl)-MeIle-MeIle-Gly-MeVal-Tyr(tert-butyldimethylsilyl)-OH The product of step a) above is reacted as described under Example 52 for the preparation of the starting material therefor. The product is a colourless foam.

The compounds of Examples 2 to 50 and 69 to 83 can also be obtained according to process f) (ring closure) in a manner analogous to Examples 52 and 64 to 68, whereby for the compounds wherein R$_4$ is carboxy the carboxy group is transiently protected.

Example 69:
Cyclo-[Pec-MeVal-Val-MeAsp(β-O-benzyl)-MeIle-MeIle-Gly-MeVal-Tyr(n-propyloxy)-Phe; R$_4$=—COO-benzyl]
[process variant g); hydrogenation at R$_3$ group]

38 mg Cyclo-[Pec-MeVal-Val-MeAsp(β-O-benzyl)-MeIle-MeIle-Gly-MeVal-Tyr(allyl)-D-Lact] (see Example 41) are dissolved in 3 ml of ethanol and after addition of a spoontip of 10% palladium on charcoal hydrogenation is effected at room temperature and normal pressure. After 4 hours the catalyst is filtered off and the liltrate is concentrated. The residue is chromatographed over silicagel using hexane/ethyl acetate as an eluant. The title compound is obtained (colourless foam):
NMR:
1:1 mixture of conformers
2.70, 2.78, 2.78, 2.82, 2.96, 3.00, 3.04, 3.07, 3.07, 3.36 (N—CH$_3$), OCH$_3$ is missing, 5.01, 5.09 (COOCH$_2$—), 7.20–7.40 (Ar).

The compound of Example 12 can also be obtained according to process g) (hydrogenation) in a manner analogous to Example 69.

Example 70:
Cyclo-[Pec-MeVal-Val-MehSer-MeIle-MeIle-Gly-MeVal-Tyr(Me)-D-Lact]
[R$_1$, R$_2$, R$_3$, R$_5$, X, Y, C$_{10}$=as for 1st compound of Example 1; R$_4$=hydroxymethyl]
[process variant h); carboxy group reduction]

Chloromethylene-dimethylammonium chloride (prepared from 0.05 ml of dimethylformamide and 0.25 ml of oxalyl chloride in 15 ml of dichloromethane) and 375 mg first title compound of Example 1 are stirred for one hour at 0° to 4° in 5.5 ml of tetrahydrofuran and 1.5 ml of acetonitrile. A solution of 76 mg sodium hotsnare is 4 ml of dimethylformamide is then added dropwise at −70° and stirring is pursued for 1.5 hour at −70°. The temperature of the solution is allowed to rise to −10°, 4 ml of saturated aqueous ammonium chloride solution are added and the solution is extracted between water and acetic acid ethyl ester. The organic phase is evaporated to dryness. The crude product is chromatographed over silicagel using acetic acid ethyl ester as an eluant. The title compound is obtained (amorphous):
NMR:
3:1 mixture of conformers
Main component: 2.50, 2.78, 2.87, 2.95, 3.44 (N—CH$_3$), 3.78 (OCH$_3$).

Example 71:
Cyclo-[Pec-MeVal-Val-MeAsp(β-al)-MeIle-MeIle-Gly-MeVal-Tyr(Me)-D-Lact]
[R$_1$, R$_2$, R$_3$, R$_5$, X, Y, C$_{10}$=as for 1st compound of Example 1; R$_4$=formyl]
[process variant h); carboxy group reduction]

The title compound (colourless solid) is obtained in a manner analogous to Example 70. The course of the reaction is followed using thin-layer chromatography in order to avoid over-reduction to the alcohol.
NMR:
1.5:1 mixture of conformers
Main component: 2.63, 2.78, 3.02, 3.04, 3.39 (N—CH$_3$), 3.81 (OCH$_3$), 9.70 (dd, J$_1$=3.5 Hz, J$_2$=1.5 Hz, CHO).
Other component: 2.69, 2.78, 2.88, 2.90, 3.08 (N—CH$_3$), 3.75 (OCH$_3$), 9.75 (d, br, J=3 Hz, CHO).

Example 72:
Cyclo-[Pec-MeVal-Val-MehSer(Ac)-MeIle-MeIle-Gly-MeVal-Tyr(Me)-D-Lact]
[R$_1$, R$_2$, R$_3$, R$_5$, X, Y, C$_{10}$=as for 1st compound of Example 1; R$_4$=acetoxymethyl]
[process variant i); acylation]

123 mg title compound of Example 70 are stirred at room temperature with 0.1 ml of acetic acid anhydride and 0.1 mg dimethylaminopyridine for 15 hours. The resultant mixture is concentrated and treated with 0.1 N HCl/acetic acid ethyl ester. The title compound (M.P. 184°–195°; white crystals) is recovered from the organic phase after drying (MgSO$_4$) and solvent evaporation:

NMR:
4:1 mixture of conformers
Main component: 1.38 (10-CH$_3$), 1.97 (CH$_3$CO), 2.58, 2.77, 2.95, 3.00, 3.37 (N—CH$_3$), 3.79 (OCH$_3$).
Other component: 1.41 (10-CH$_3$), 2.04 (CH$_3$CO), 2.73, 2.77, 2.80, 2.86, 3.09 (N—CH$_3$), 3.74 (OCH$_3$).

Example 73:
cyclo-[Pec-MeVal-Val-MeAbu(γ-N$_3$)-MeIle-MeIle-Gly-MeVal-Tyr(Me)-D-Lact]
[R$_1$, R$_2$, R$_5$, X, Y, C$_{10}$=as for 1st compound of Example 1; R$_3$=p-methoxyphenyl; R$_4$=azidomethyl]
[process variant j); conversion to azide]

624 mg title compound of Example 72, 0.5 mg dimethylaminopyridine and 0.44 mg mesyl chloride are stirred for 3 hours at 0° to 5° in 9 ml of pyridine. The solution is evaporated to dryness, the residue treated with 5 ml of water and the solution again evaporated to dryness. The residue is stirred for 15 hours at room temperature with 155 mg sodium azide in 9 ml of dimethylformamide. The mixture is then treated with acetic acid ethyl ester/water, the organic phase is dried (MgSO$_4$) and the solvent evaporated. The crude product is purified by chromatography over silicagel using acetic acid ethyl ester as an eluant. The title compound is obtained (colourless crystals, M.P. 216°–223°).

Example 74:
Cyclo-[Pec-MeVal-Val-MeAbu(γ-Cl)-MeIle-MeIle-Gly-MeVal-Tyr(Me)-D-Lact]
[R$_1$, R$_2$, R$_5$, X, Y, C$_{10}$=as for 1st compound of Example 1; R$_3$=p-methoxypheny; R$_4$=chloromethyl]
[process variant k); halogenation]

111 mg title compound of Example 72 and 154 mg tosyl chloride are stirred for 64 hours at 50° to 60° in 7 ml of pyridine. 10 ml of water are added, the solution is concentrated under reduced pressure to about 2 to 3 ml and extracted with acetic acid ethyl ester. The organic phase is successively washed with water, 0.1 N HCl and saturated aqueous NaHCO$_3$ solution, dried over MgSO$_4$ and evaporated to dryness. The resultant crude product is purified by chromatography over silicagel. The title compound is obtained (colourless resin):
NMR:
2:1 mixture of conformers
Main component: 2.60, 2.78, 2.93, 3.02, 3.37 (N—CH$_3$), 3.80 (OCH$_3$).
Other component: 2.72, 2.78, 2.81, 2.86, 3.08 (N—CH$_3$), 3.74 (OCH$_3$).

The following compounds of formula I are obtained in a manner analogous to Example 72 [process variant i)i acylation] starting from the title compound of Example 70 (R$_1$, R$_2$, R$_3$, R$_5$, X, Y, C$_{10}$=as for 1st compound of Example 1):

| Example No. | R$_4$ | Characterization data |
| --- | --- | --- |
| 75 | —CH$_2$OCO(CH$_2$)$_2$COOH | colourless resin; NMR* |
| 76 | —CH$_2$OCO—(2-COOH—Phe) | colourless resin; NMR* |

*NMR:
Example 75: 4:1 mixture of conformers
Main component: 2.78, 2.78, 2.98, 3.03, 3.30 (N—CH$_3$), 3.80 (OCH$_3$), 2.57 (COCH$_2$CH$_2$CO).
Example 76: 1:1 mixture of conformers
Main component: 2.57, 2.59, 2.79, 2.79, 2.81, 2.88, 2.89, 3.00, 3.06, 3.08 (NCH$_3$), 3.74, 3.80 (OCH$_3$), 7.2–7.8 (Ar).

Example 77:
Cyclo-[Pec-MeVal-MeVal-MeAsp(β-OCH$_3$)-MeIle-MeIle-Sar-MeVal-MeTyr(Me)-D-Lact]
[R$_1$, R$_2$, X, Y, C$_{10}$=as for 1st compound of Example 1; R$_3$=p-methoxyphenyl; R$_4$=—COOCH$_3$; R$_5$=methyl]
[process variant m); permethylation]

To 337 mg cyclo-[Pec-MeVal-Val-MeAsp-MeIle-MeIle-Gly-MeVal-Tyr(Me)-D-Lact] (first title compound of Example 1) and 317 mg 18-Crown-6 (1,4,7,10,13,16-hexaoxacyclooctadecane) dissolved in 10 ml of dry tetrahydrofuran is added under argon at −20° potassium hydride (240 mg of a commercial 20% suspension in oil are made essentially oil-free by digestion with hexane). After 5 minutes of stirring at −20°, 0.25 ml of methyl iodide is added dropwise at −20°. After 48 hours at −20° the reaction mixture is carefully poured onto ice-water, acidified with 0.1N hydrochloric acid and extracted with ethyl acetate. The organic phase is washed with water, dried over sodium sulfate and the solvent is removed under reduced pressure. The crude product is chromatographed over silicagel using ethyl acetate as an eluant. The title compound is obtained (colourless foam):

NMR:
Single component: 2.46, 2.73, 2.76, 2.83, 2.91, 2.97, 3.03, 3.09 (N—$CH_3$), 3.62 ($COOCH_3$), 3.81 ($OCH_3$).

The following compound of formula I is obtained in a manner analogous to Example 77, starting from the corresponding compound of formula I wherein $R_5$ is hydrogen [$R_1$, $R_2$, X, Y, $C_{10}$=as for 1st compound of Example 1; $R_3$=p-methoxyphenyl]:

| Example No. | $R_4$ | $R_5$ | Characterization data |
|---|---|---|---|
| 78 | —COOtBu | methyl | colourless foam; NMR* |

*NMR:
Single component: 1.43 (tBu), 2.46, 2.73, 2.76, 2.84, 2.91, 2.98, 3.02, 3.08 (n-$CH_3$), 3.81 ($OCH_3$).

Example 79:
Cyclo-[Pec-MeVal-Val-MeAla-MeIle-MeIle-Gly-MeVal-Tyr(Me)-D-Lact]
[$R_1$, $R_2$, $R_3$, $R_5$, X, Y, $C_{10}$=as for 1st compound of Example 1; $R_4$=—H]
[process variant n); decarboxylation]

900 mg Cyclo-[Pec-MeVal-Val-MeAsp(β-O-phenylselenyl)-MeIle-MeIle-Gly-MeVal-Tyr(Me)-D-Lact] are heated to boiling temperature in 36 ml of xylene and the mixture is reacted with 0.325 ml of tributyl tin hydride and 1 ml of azoisobutyronitrile. After 2 hours of boiling under reflux the solution is evaporated and the residue chromatographed over silicagel using dichloromethane/diisopropylether/methanol 10:4:1 as an eluant. The title compound is obtained (colourless crystals from hexane/ethyl acetate; M.P. 158°).

The starting material is obtained as follows:

To a solution of chloromethylene-dimethylammonium chloride (prepared from 0.38 ml of dimethylformamide and 0.14 ml of oxalyl chloride in 2.5 ml of acetonitrile) is added dropwise at −30° 337 mg first title compound of Example 1 dissolved in 2.5 ml of acetonitrile, followed by 0.75 ml of pyridine and 1.5 ml of a 0.35M solution of phenylselenylhydride in benzene. The temperature is allowed to rise to −10° and stirring is continued for 18 hours at that temperature. The reaction mixture is added onto ice-cold 0.1N hydrochloric acid and extracted thrice with ethyl acetate. The organic phase is washed 5 times with water, dried over sodium sulfate and the solvent is evaporated under reduced pressure. The crude product is chromatographed over silicagel using dichloromethane/diisopropylether/methanol 10:4:1 as an eluant. Cyclo-[Pec-MeVal-Val-MeAsp(β-O-phenylselenyl)-MeIle-MeIle-Gly-MeVal-Tyr(Me)-D-Lact] is obtained (colourless solid).

Example 80:
Cyclo-[Pec-MeVal-Val-Sar[(S,E)-(3tert-butoxycarbonyl)prop-2-enyl]-MeIle-MeIle-Gly-MeVal-Tyr(Me)-D-Lact]
[$R_1$, $R_2$, $R_5$, X, Y, $C_{10}$=as for 1st compound of Example 1; $R_3$=p-methyloxyphenyl; $R_4$=—CH=CH—COOtBu]
[process variant o); formyl conversion]

0.11 g title compound of Example 71 and 0.05 g tert-butoxycarbonylmethylentriphenylphosphorane are stirred for 20 hours in 4 ml of toluene at room temperature. The solvent is evaporated under reduced pressure. The residue is chromatographed over silicagel using hexane/ethyl acetate 1:4 as an eluant. The title compound is obtained (colourless solid; M.P. 176°–178°);

NMR:
3:1 mixture of conformers
Main component: 1.39 (tBu), 2.65, 2.78, 3.01, 3.04, 3.38 (N—$CH_3$), 3.79 ($OCH_3$), 5.83 (d, J=15 Hz, olefinic H).
Other component: 1.40 (tBu), 2.71, 2.79, 2.83, 2.85, 3.08 (N—$CH_3$), 3.73 ($OCH_3$), 5.80 (d, J=15 Hz, olefinic H).

Example 81:
Cyclo-[Pec-MeVal-Sar[(S)-(B-tert-butoxycarbonyl)propyl]-MeIle-MeIle-Gly-MeVal-Tyr(Me)-D-Lact]
[$R_1$, $R_2$, $R_5$, X, Y, $C_{10}$=as for 1st compound of Example 1; $R_3$=p-methoxyphenyl; $R_4$=—$(CH_2)_2$COOtBu]
[process variant p); hydrogenation at $R_4$ group]

0.035 g of title compound of Example 80 is dissolved in 3 ml of ethanol and treated with a spoontip of palladium 10% on charcoal. Hydrogenation is effected for 18 hours at normal pressure under hydrogen atmosphere. The catalyst is filtered off, the solution evaporated to dryness. The residue is purified by treatment with diethylether/petroleum ether, the title compound is obtained (colourless solid; M.P. 159°–162°);

NMR:
4:1 mixture of conformers
Main component: 1.39 (tBu), 2.59, 2.79, 2.96, 2.99, 3.40 (N—$CH_3$), 3.79 ($OCH_3$).
Other component: 1.39 (tBu), 2.69, 2.84, 2.86, 3.02, 3.11 (N—$CH_3$), 3.74 ($OCH_3$).

Example 82:
Cyclo-[Pec-MeVal-Val-MeAsp(β-L-valinolamide)-MeIle-MeIle-Gly-MeVal-Tyr(Me)-D-Lact]
[$R_1$, $R_2$, $R_5$, X, Y, $C_{10}$=as for 1st compound of Example 1; $R_3$=p-methoxyphenyl

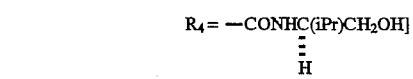

[process variant deprotection]

0.22 g Cyclo-[Pec-MeVal-Val-MeAsp[β-L-valinol(O-tert-butyl-dimethylsilylether)amide ]-MeIle-MeIle-Gly-MeVal-Tyr(Me)-D-Lact] (compound of Example 34) are dissolved in 10 ml of acetonitrile, the solution is cooled to 0° and treated with 0.5 ml of 40% aqueous hydrofluoric acid solution. After one hour the temperature is allowed to rise to room temperature and left at that temperature until the starting material has been consumed (control via thin-layer chromatography). The reaction mixture is then poured onto ice-water, extracted thrice with ethyl acetate, the organic phase is washed once with saturated sodium hydrogen carbonate solution and thrice with water, dried over sodium sulfate and the solvent is evaporated under reduced pressure. The residue is purified by chromatography over silicagel using hexane/ethyl acetate 1:5 as an eluant. The title compound is obtained (colourless solid; M.P. 161°163°);

NMR:
3:1 mixture of conformers

Main component: 2.68, 2.78, 2.84, 2.93, 3.17 (N—$CH_3$), 3.77 ($OCH_3$).
Other component: 2.58, 2.79, 2.99, 3.00, 3.43 (N—$CH_3$), 3.81 ($OCH_3$).

The following compound of formula I is obtained in a manner analogous to Example 82 starting from the compound of Example 63 [$R_1$, $R_2$, $R_5$, X, Y=as for 1st compound of Example 1; $R_3$=p-methoxyphenyl; $C_{10}$ has the L-configuration];

| Example No. | $R_4$ | Characterization data |
| --- | --- | --- |
| 83 | H<br>—CONHC(iPr)$CH_2$OH | colourless solid; NMR* |

*NMR:
3:1 mixture of conformers
Main component: 2.58, 2.61, 2.63, 3.09, 3.18(N—$CH_3$), 3.80($OCH_3$).
Other component: 2.76, 2.82, 2.83, 2.87, 3.06(N—$CH_3$), 3.76($OCH_3$).

The compounds of the invention possess pharmacacological activity. They are, therefore, useful as pharmaceuticals.

They possess anti-fungal activity. They are thus useful in treating diseases and infections caused by yeasts and yeast-like fungi.

In particular they show inhibitory activity in vitro and in vivo against various yeasts and yeast-like fungi but no activity could be determined against suitable representatives of gram-positive and gram-negative bacteria employing known methods.

In series dilution tests effected in malt extract medium with incubation at 27° C. for 48 to 72 hours the minimum inhibitory concentrations (MIC) are from about 1.5 mg/ml to about 25 mg/ml.

This activity can also be demonstrated in vivo on rats intravaginally infected with Candida. In this test ovarectomised rats which have been pretreated with oestradiol benzoate are infected vaginally and then treated parenterally or perorally on 2 successive days. The success of treatment is determined by the presence or absence of fungus in the vagina. Systemic activity is detected after i.p. and p.o. treatment in a dosage range of from about 25 mg/kg to about 300 mg/kg body weight. Local treatment results in cure at a concentration of from about 0.1% to about 1%.

For the above-mentioned use the dosage will of course vary depending upon the compound employed, mode of administration and condition to be treated. With larger mammals, satisfactory results are generally obtained when administering at a daily dosage of from about 300 mg to about 3000 mg, conveniently given in unit dosages one to four times daily or in sustained release form.

Further, the compounds of the invention possess activity in increasing sensitivity to, or in increasing the efficacy of, chemotherapeutic drug therapy. They are thus useful in reversing chemotherapeutic drug resistance of varying types, e.g. acquired or innate, or in increasing sensitivity to administered drug therapy. Forms of chemotherapeutic drug therapy to which the present invention is applicable include, for example, anti-parasitic, e.g. anti-vital, anti-bacterial, anti-fungal or anti-protozoal chemotherapy such as e.g. in the therapy of malaria, and in particular anti-cancer or anti-tumor, anti-neoplastic or cytostatic chemotherapy.

They are accordingly useful e.g. as a means of reducing regular chemotherapeutic dosage levels, for example in the case of anti-neoplastic or cytostatic drug therapy, as a means of decreasing overall drug toxicity and, more especially, as a means of reversing or reducing resistance, including both inherent and acquired resistance to chemotherapy.

This activity is evidenced in the following test methods:
1. Restoration of sensitivity to antineoplastic/cytotoxic, anti-tumor drug substances (in vitro) (described in EP 296122):

In the above test model the compounds of the invention are effective in increasing sensitivity to CTDS (cancer therapeutic drug substances), e.g. DR (daunorubicin), VC (vincristine), AM (adriamycin), etc. at a dosage of from 0.1 µg/ml to 1.0 µg/ml or from 1 µM to 5 µM.

2. Restoration of sensitivity to antineoplastic/cytotoxic, anti-tumor drug substances (in vivo) (described in EP 296122):

Results obtained show no significant difference in mean survival time between groups 1 (no drug-substance therapy/no test substance), 2 (drug-substance therapy/no test substance) and 3 (no drug-substance therapy/test substance). In group 4 (drug-substance therapy+test substance) receiving test substance at dosages of test substance of from 10 mg/kg to 100 mg/kg p.o. daily, substantial increase in survival time (e.g. of the order of 2 to 3 fold or greater) as compared with both groups 2 and 3 is observed.

Dosages to be employed in practicing the above reversal of chemotherapeutic drug resistance use, of course, vary depending e.g. on the compound used, the condition to be treated (for example the disease type and the nature of resistance), the effect desired and the mode of administration. In general, however, satisfactory results are obtained on administration orally at dosages of the order of from about 1 mg/kg to about 20 mg/kg daily or up to 50 mg/kg daily, e.g. of the order of from about 5 mg/kg to about 10 mg/kg or up to 15 mg/kg daily administered once or in divided doses two to four times per day, or on administration parenterally, e.g. intravenously, for example by i.v. drip or infusion, at dosages of the order of from about 0.5 mg/kg to about 7.5 mg/kg or up to 10 mg/kg daily, e.g. of the order of from 1.5 mg/kg or 2.0 mg/kg up to 5.0 mg/kg daily. Suitable daily dosages in the large mammal are of the order of from about 50 mg to about 1000 mg or up to 2500 mg p.o., e.g. of the order of from about 250 mg to about 500 mg or up to 600 mg p.o., or of the order of from about 25 mg to about 375 mg or up to 500 mg i.v., e.g. of the order of from about 75 mg to about 100 mg or up to 250 mg i.v.

The preferred dosage range is from about 10 mg/kg to about 50 mg/kg p.o. daily.

Whilst the chemotherapeutic drug resistance reversing activity is the main activity of the compounds of the invention and the compounds of the invention normally possess the type of activity which is usually associated with compounds of the structural class of cyclosporins, namely immunosuppressant activity, only to an insignificant degree or not at all, some of the compounds of the invention may possess some such immunosuppressant and anti-inflammatory properties.

This activity may e.g. be determined according to the test methods described in EP 315978.

These particular compounds of the invention are therefore useful as immunosuppressant and antiinflammatory agents in the prevention and treatment of conditions requiring immunosuppression and of inflammatory conditions.

The compounds of the invention may be administered systemically or topically, by any conventional route, in particular enterally, e.g. orally, e.g. in the form of tablets or capsules, or topically, e.g. in the form of lotions, gels or creams. A tablet contains e.g. about 50 parts (w/w) of a compound of the invention and about 200 parts (w/w) of an inert carrier or diluent.

Pharmaceutical compositions comprising a compound of the invention as defined above in association with at least one pharmaceutical acceptable carrier or diluent may be manufactured in conventional manner by mixing with a pharmaceutically acceptable carrier or diluent.

The acute toxicity of the compounds of the invention in the mouse is above 100 mg/kg p.o.

Preferred in the above reversal of chemotherapeutic drug resistance reversing use are compounds possessing a relatively low level or no immunosuppressant and anti-inflammatory activity, e.g the compounds of formula I wherein $R_4$ is other than carboxy. Particularly preferred in this indication are the compounds of Example 22 and especially of Example 52, i.e.cyclo-[Pec-MeVal-Val-MeAsp (β-O-tert-butyl)-MeIle-MeIle-Gly-MeVal-Tyr(Me)-L-Lact].

Preferred in the above anti-fungal use are especially the compounds of formula Ia. Particularly preferred in this indication are the title compounds of Example 1, especially the first title compound of Example 1.

wherein $R_1$ and $R_2$ are methyl, $R_3$ is para-methoxyphenyl $R_4$ is carboxy, each $R_5$ is hydrogen, X is oxygen, Y is a direct bond, and the carbon atom in the 10 position has the D-configuration.

2. A pharmaceutical composition comprising a therapeutically effective amount of the compound according to claim 1 and a pharmaceutically acceptable carrier therefor.

3. A method of treating fungus infections in a subject in need of said treatment, which comprises administering to said subject an anti-fungal effective amount of the compound according to claim 1.

4. The compound of formula I

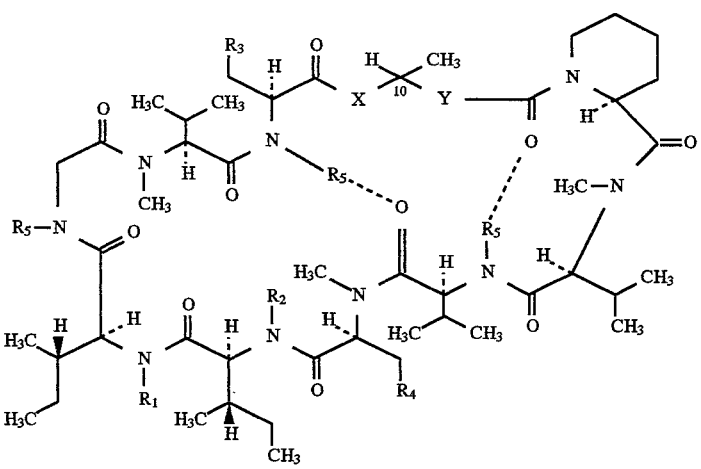

We claim:

1. The compound of formula I

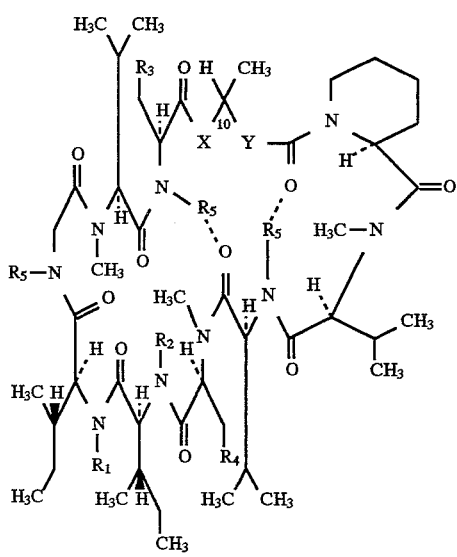

wherein $R_1$ and $R_2$ are methyl, $R_3$ is para-methoxyphenyl, $R_4$ is tert-butoxycarbonyl, each $R_5$ is hydrogen, X is oxygen, Y is a direct bond, and the carbon atom in the 10 position has the L-configuration.

5. A pharmaceutical composition comprising a therapeutically effective amount of the compound according to claim 4 and a pharmaceutically acceptable carrier therefor.

6. A method of treating fungus infections in a subject in need of said treatment, which comprises administering to said subject an anti-fungal effective amount of the compound according to claim 4.

* * * * *